(12) United States Patent
Wong et al.

(10) Patent No.: US 6,774,140 B1
(45) Date of Patent: Aug. 10, 2004

(54) IMINOCYCLITOL INHIBITORS OF HEXOAMINIDASE AND GLYCOSIDASE

(75) Inventors: Chi-Huey Wong, Rancho Santa Fe, CA (US); Jungie Liu, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 09/980,869

(22) PCT Filed: May 11, 2000

(86) PCT No.: PCT/US00/13048
§ 371 (c)(1),
(2), (4) Date: Feb. 12, 2002

(87) PCT Pub. No.: WO00/68194
PCT Pub. Date: Nov. 16, 2000

Related U.S. Application Data
(60) Provisional application No. 60/133,549, filed on May 11, 1999.

(51) Int. Cl.$^7$ ........................ A61K 31/40; C07D 207/12
(52) U.S. Cl. .......................................... 514/425; 548/556
(58) Field of Search ................................ 514/425, 422; 548/556, 518

(56) References Cited

U.S. PATENT DOCUMENTS
5,595,981 A * 1/1997 Barta et al.

OTHER PUBLICATIONS
STN International ®CAPLUS Database, Accession No. 1997:530913; Wrodnigg et al. Tetrahedron Letters (1997) 38 (31), 5463–5466, abstract.*
Wong, et al., "Enzymes in Organic Synthesis: Application to the Problems of Carbohydrate Recognition (Part 1)", *Angew. Chem. Int. Ed. Engl.* 34:412–432 (1995).
Wong, et al., "Enzymes in Organic Synthesis: Application to the Problems of Carbohydrate Recognition (Part 2)", *Angew. Chem. Int. Ed. Engl.* 34: 521–546 (1995).
Heightman, et al., "Synthesis of Galactose– and N–Acetylglucosamine–Derived Tetrazoles and Their Evaluation as β–Glycosidase Inhibitors", *Helvetica Chem. Acta* 78: 514–532 (1995).
Wong, et al., "Synthesis and Evaluation of Homoazasugars as Glycosidase Inhibitors", *J. Org. Chem.* 60: 1492–1501 (1995).
Hiranuma, et al., "Synthesis and Inhibition Analysis of Five–Membered Homoazasugars from D–Arabinofuranose via an $S_N2$ Reaction of the Chloromethylsulfonate", *Tetrahedron Lett.* 36: 8247–8250 (1995).
Ganem, "Inhibitors of Carbohydrate–Processing Enzymes: Design and Synthesis of Sugar–Shaped Heterocycles", *Acc. Chem. Res.* 29: 340–347 (1996).
Picasso, "Azasugar Glycosidase Inhibitors: Useful Tools for Glycobiologists", *CHIMIA* 50: 648–649 (1996).
Ichikawa, et al., "1–N–Iminosugars: Potent and Selective Inhibitors of β–Glycosidases", *J. Am. Chem. Soc.* 120: 3007–3018 (1998).

Hettkamp, et al., "Purification by affinity chromatography of glucosidase 1, an endoplasmic reticulum hydrolase involved in the processing of asparagine–linked oligosaccharides", *Eur. J. Biochem.* 142: 85–90 (1984).
Fleet, et al., "Potent Competitive Inhibition of α–Galactosidase and α–Glucosidase Activity by 1,4–Dideoxy–1,4–Iminopenitols: Syntheses of 1,4–Dideoxy–1,4–Imino–D–Lyxitol and of Both Enantiomers of 1,4–Dideoxy–1,4–Iminoarabinitol", *Tetrahedron Lett.* 26: 3127–63130 (1985).
Schweden, et al., "Characterization of Calf Liver Glucosidase 1 and Its Inhibition by Basic Sugar Analogs", *Archives Biochem. Biophys.* 248: 335–340 (1986).
Pederson, et al., "A Combined Chemical and Enzymatic Procedure for the Synthesis of 1–Deoxynojirimycin and 1–Deoxymannojirimycin", *Tetrahedron Lett.* 29: 4645–4648 (1988).
Ziegler, et al., "Enzyme–Catalyzed Synthesis of 1–Deoxymannojirimycin, 1–Deoxynojirimycin, and 1,4–Dideoxy–1, 4–imino–D–arabinitol", *Angew Chem. Int. Ed. Engl.* 27: 716–717 (1988).
Fleet, et al., "Inhibition of HIV replication by amino–sugar derivatives", *FEBS Letters* 237: 128–132 (1988).
von der Osten, et al., "Use of a Recombinant Bacterial Fructose–1,6–diphosphate Aldolase in Aldol Reactions: Preparative Syntheses of 1–Deoxynojirimycin, 1–Deoxymannojirimycin, 1,4–Dideoxy–1,4–imino–D–arabinitol, and Fagomine", *J. Am. Chem. Soc.* 111: 3924–3927 (1989).
Kajimoto, et al., "Enzyme–Catalyzed Aldol Condensation for Asymmetric Synthesis of Azasugars: Synthesis, Evaluation, and Modeling of Glycosidase Inhibitors", *J. Am. Chem. Soc.* 113: 6187–6196 (1991).
Liu, et al., "Use of Dihydroxyacetone Phosphate Dependent Aldolases in the Synthesis of Deoxyazasugars", *J. Org. Chem.* 56: 6280–6289 (1991).
Pan, et al., "D–Mannonolactam Amidrazone", *J. Biol. Chem.* 267: 8313–8318 (1992).
Takaoka, et al., "Inhibition of N–Acetylglucosaminyltransfer Enzymes: Chemical–Enzymatic Synthesis of New Five–Membered Acetamido Azasugars", *J. Org. Chem.* 58: 4809–4812 (1993).
Hughes, et al., "Deoxynojirimycin: Synthesis and Biological Activity", *Nat. Product Rep.*: 135–162 (1994).
Schumacher–Wandersleb, et al., "Preparation of the N–Acetylglucosaminidase Inhibitor 1–Acetamido–1,2, 5–trideoxy–2,5–imino–D–glucitol from Methyl α–D–Mannopyranoside", *Liebigs Ann. Chem.*: 555–561 (1994).
Wang, et al., "Remarkable Stereoselectivity in the Inhibition of α–Galactosidase from Coffee Bean by a New Polyhydroxypyrrolidine Inhibitor", *Angew. Chem. Int. Ed. Engl.* 33: 1242–1244 (1994).

\* cited by examiner

*Primary Examiner*—Alan L. Rotman
*Assistant Examiner*—Sonya Wright
(74) *Attorney, Agent, or Firm*—Donald G. Lewis

(57) ABSTRACT

Designed iminocylitols that have potent inhibition activity with respect to hexominidases and glycosides are disclosed.

13 Claims, 20 Drawing Sheets

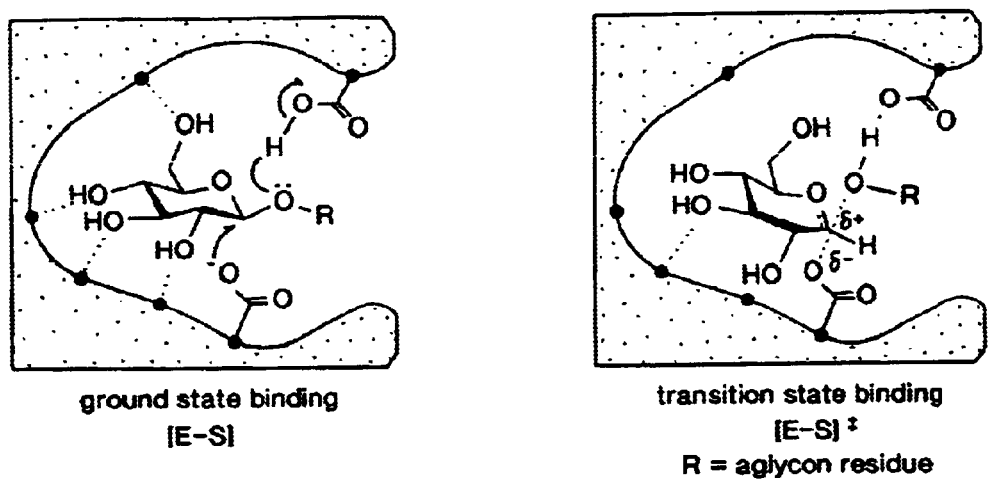
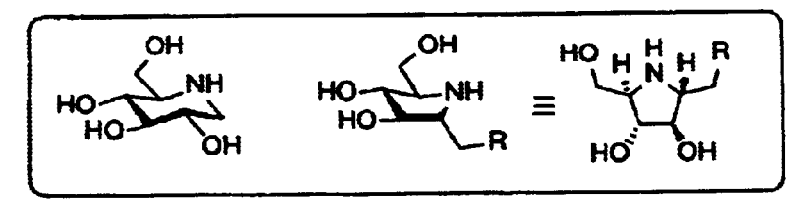
FIG. 1

| | $K_i$ (µM) | | | | |
|---|---|---|---|---|---|
| | α-glucosidase[a] | β-glucosidase[b] | β-N-acetylglucosaminidase | β-N-acetylhexosaminidase | |
| compd | Saccaromyces sp | sweet almond | bovine kidney[c] | human placenta A[d] | p[e] |
| 1[f] | 330 | 50 | -[h] | - | - |
| 2[f] | 28 | 2.6 | - | - | - |
| 3 | 380 | *[g] | $2.9 \times 10^{-1}$ | $2.2 \times 10^{-1}$ | $2.6 \times 10^{-1}$ |
| 4 | ni | ni | $1.1 \times 10^{-1}$ | $1.4 \times 10^{-1}$ | $8.0 \times 10^{-2}$ |
| 5 | ni | ni | 1.3 | $5.1 \times 10^{-1}$ | $2.4 \times 10^{-1}$ |
| 6 | * | 2.2 | * | - | - |
| 7 | * | 45 | * | - | - |
| 8 | ni | 120 | ni[i] | - | - |
| 9 | 53 | 37 | - | - | - |

FIG. 3

[a] $K_m$ = 0.30 mM, $V_{max}$ = 0.7 (µM/s)/mg. [b] $K_m$ = 3.2 mM, $V_{max}$ = 3.2 (µM/s)/mg. [c] $K_m$ = 4.1 mM, $V_{max}$ = 6.4 (µM/s)/mg. [d] $K_m$ = 2.5 mM, $V_{max}$ = 2.1 (µM/s)/mg. [e] $K_m$ = 2.8 mM, $V_{max}$ = 2.3 (µM/s)/mg. [f] Preliminary assay result using photometric assay gave $K_i$ values: 430 and 18 µM for compound 1 and 7.2 and 7.6 µM for compound 2 toward α-glucosidase and β-glucosidase, respectively. See also refs 6a and 19. [g] *: poor inhibitor with IC$_{50}$ above 0.5 mM. [h] -: not tested. [i] ni: not inhibitor.

a NH₄OAc - NaBH₃CN / MeOH;  b (Boc)₂O - Et₃N / CH₂Cl₂;  c 1) Pd/C / MeOH - HCl, 2) TFA.

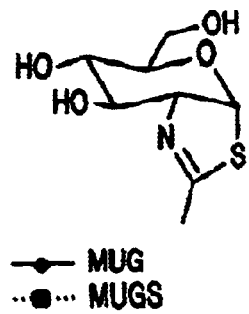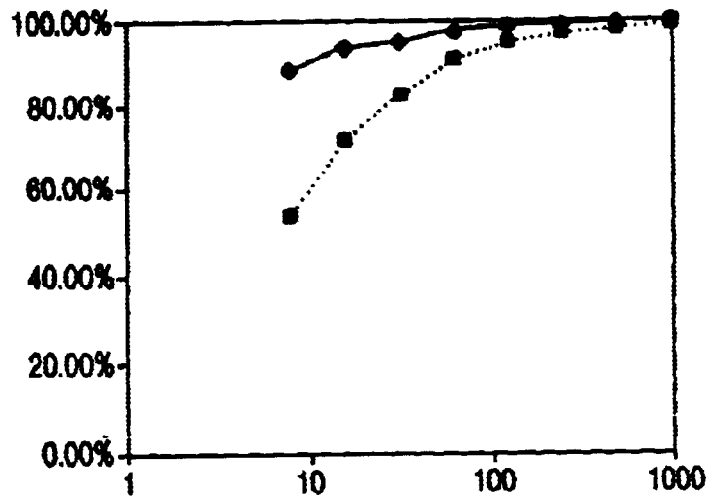
FIG. 13A
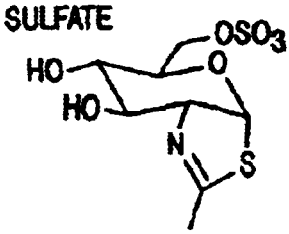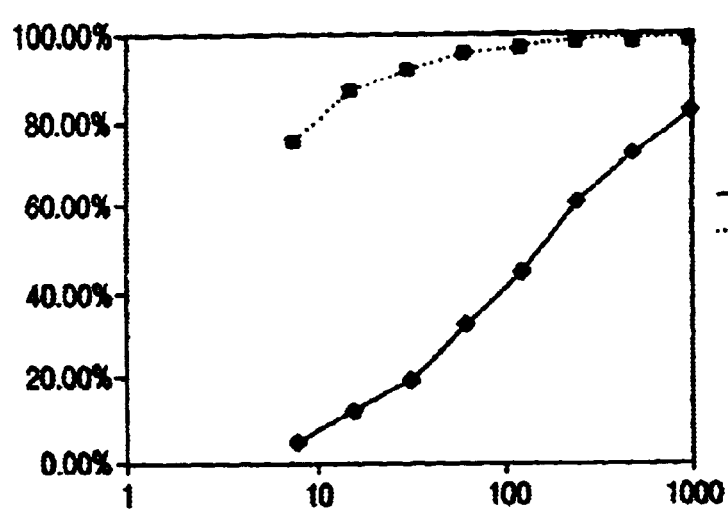
FIG. 13B a. Me₃S⁺I/NaH, DMSO/THF; b. NaN₃, acetone/H₂O, 82% from 110: c. MsCl, Pyr. 96%; d. HMTA, NaI/EtOH; HCl, 65°C; e. isopropenyl acetate, 85% from 113; f. O₃, Me₂S; g. DHAP, RAMA, pH=6.5; acid pase 37°C, pH=4.7; 44% for (R), 30% for (S); h. Pd-C/H₂, 80%; i. CH₂O, Pd-C/H₂, 90%.

a. TBDMSOTf, TEA, 0 °C, DMF, 1.0 h, 90%; b. BnBr, NaH, 0 °C - 25 °C, 90%; c. TBAF, THF, 0 °C - 25 °C, 4h, 80%; d. SO₃/Pyr, pyridine, 25 °C, 80%; e. Pd(OH)₂/C, H₂, 75%

IMINOCYCLITOL INHIBITORS OF HEXOAMINIDASE AND GLYCOSIDASE

This application is a 371 of PCT/US00/13048 filed May 11, 2000, which claims benefit of 60/133,549, filed May 11, 1999.

This invention was made with government support under Contract No. 9310081 by the National Science Foundation. The government has certain rights in the invention.

TECHNICAL FIELD

The present invention relates to the inhibition of hexoaminidase and glycosidase. More particularly, the present invention relates to the selective inhibition of hexoaminidases and glycosidases using designed iminocylitols.

BACKGROUND

Enzymatic hydrolysis of glycosidic bonds generally takes place via general acid-base catalyses that require two critical residues, a proton donor and a nucleophile. The process is illustrated in FIG. 1. Five- or six membered iminocyclitols carrying hydroxyl groups with specific orientation and a secondary amine have been used to mimic the shape and charge of the transition state of the reaction and have been shown to be potent inhibitors of such enzymes (T. A. Beyer, et al., *J. Biol. Chem.* 1979, 254, 12531–12541; H. Paulsen, et al., *Adv. Carbohydr. Chem. Biochem.* 1968, 23, 115–232; A. B. Hughes, et al., *J. Nat. Prod. Rep.* 1994, 135–162; C.-H. Wong, et al., *Angew. Chem., Int. Ed. Engl.*, 1995, 34, 412–432 and 521–546; B. Ganem, *Acc. Chem. Res.* 1996, 29, 340–347; S. Picasso, *Chimia*, 1996, 50, 648–649; L. A. G. M. van den Broek, in Carbohydr. Drug Des. 1997, Eds by Z. J. Witczak, et al., Dekker, New York, pp 1–37 and pp471–493; G. W. Fleet, et al., *Tetrahedron Lett.* 1985, 26, 3127–3130; Y. T Pan, et al., *J. Biol. Chem.* 1992, 267, 8313–8318; c) T. D. Heightman. et al., *Helvetica Chim. Acta* 1995, 78, 514–532; and Y. Ichikawa, et al., *J. Am. Chem. Soc.* 1998, 120, 3007–3018). One process for synthesizing iminocyclitols is based on aldolase-catalyzed reactions (R. L. Pederson, et al., *Tetrahedron Lett.* 1988, 29, 46454648; T. Ziegler, et al., *Angew. Chem. Int. Ed. Engl.* 1988, 27, 716–717; C. H. von der Osten, et al., *J. Am. Chem. Soc.* 1989, 111, 2924–3927; T. Kajimoto, et al., *J. Am. Chem. Soc.* 1991, 113, 6187–6196; K. K.-C. Liu, et al., *J. Org. Chem.* 1991, 56, 6280–6289; and Y. F. Wang, et al., *Angew. Chem. Int. Ed. Engl.* 1994, 33, 1242–1244). Another process for synthesizing iminocyclitols is based on multi-step chemical transformations (S. Hiranuma, et al., *Tetrahedron Lett.* 1995, 36, 8247–8250; and C.-H. Wong, et al., *J. Org. Chem.* 1995, 60, 1492–1501). A preferred method for assaying inhibition activity without using radioactive isotopes employs electrospray mass spectrometry and capillary zone electrophoresis (CZE) (S. Takayama, et al., *J. Am. Chem. Soc.* 1997, 119, 8146–8151; J. Wu, et al., *Chem. Biol.* 1997, 4, 653–657; Y. Kanie, et al., *Anal. Biochem.* 1998, 263, 240–245; R., Zeleny, et al., *Anal. Biochem.* 1997, 256, 96–101; K. B. Lee, et al., *Anal. Biochem.* 1992, 205, 108–114; and K.-B. Lee, et al., *Electrophoresis*, 1991, 12, 636–640).

Glycosidases and hexoaminidases catalyze a myriad of clinically important processes. For example, cartilage erosion in arthritic subjects results from the over-catabolism of glycosaminoglycans (GAGs) of proteoglycan (PG)-hyaluronate complex, which fills the most part in cartilage tissue. The process is illustrated in FIG. 8 The cartilage PG consists of a central protein core to which GAG side chains of chondroitin sulfate (CS) and keratan sulfate (KS) are attached together with O-linked and N-linked oligosaccharides. The PGs bind to hyaluronic acid noncovalently. The degradation of GAGs is a very complicated process, involving a multi-enzyme systems and radical reactions. It is known that subjects with arthritis have an abnormal increase of β-N-acetylhexoaminidases activities (O. Kida, *J. Jap. Orthop. Ass.* 1968, 42(6), 4010; R. W. Stephen, et al., *Biochim. Biophys. Acta* 1975, 399(1), 101; and J. J. Steinberg, et al., *Biochim. Biophys. Acta* 1983, 757(1), 47). The higher β-N-acetylhexoaminidases activity amplifies that of hyaluronidase and increases the degradation rate of GAG side chains.

What are needed are iminocyclitols having inhibitory activities against hexoaminidases and glycosidases.

SUMMARY

One aspect of the invention is directed to designed iminocyclitols and their use for the inhibition of glycosidases. A series of five membered iminocyclitols are synthesized starting from a single starting material through Wittig reaction, Sharpless epoxidation, and double inversion reactions using the chloromethanesulfonyl group as a leaving group. This versitile synthetic strategy provides a useful route to heterocycles having activity as inhibitors of glycosidases.

It is disclosed herein that the differences in the conformation and the orientation of side chains and OH groups might be the main reason for the observed higher inhibitory activity of the 2(R),5(R)-isomer 2 compared to the 2(S),5 (R)-isomer 1. Using 2 as a starting material, a number of iminocyclitols were synthesized and tested as glycosidase inhibitors using capillary electrophoresis, and the results showed remarkable specificities toward several glycosidases. Among such compounds, 6 and 3~5 were shown to be potent inhibitors of β-glucosidase and β-N-acetylglucosaminidase, respectively.

It is also disclosed herein that the amine function of compound 6 or the OH function of compound 24 may be used to make conjugates with various aglycon groups to prepare inhibitors with improved specificities. In addition, N-methylation of compound 3 is disclosed to enhance its inhibition activity with respect to specific enzymes.

Another aspect of the invention is directed to designed iminocyclitols and their use as inhibitors with respect to hexoaminidases, including the treatment for arthritis. Several forms of arthritis are characterized by abnormally high β-N-acetylhexoaminidase activity. It is disclosed herein that such forms of arthritis are treatable with designed iminocyclitols having inhibitory activity with respect to β-N-acetylhexoaminidase. Inhibition of β-N-acetylhexoaminidase activity is disclosed herein to delay and/or reduce the degradation of PG side chains and the followed cross-reactive immune response.

Two proposed mechanisms for the catalytic mechanism of the β-N-acetylhexoaminidases are illustrated in FIG. 9. The first proposed mechanism employs an oxonium ion transition state (D. E. Koshland, *Biol. Rev.* 1953, 28, 416). According to this first mechanism, there is partial positive charge on the ring oxygen atom, which is stabilized by the depronatated carboxyl group from the enzyme. A second mechanism involving the participation of the neighboring C-2 acetamido group has also been proposed (S. Knapp, et al., *J. Am. Chem. Soc.* 1996, 119, 6804). Transition states analogs corresponding to both mechanisms were synthesized and evaluated, as illustrated in FIG. 10.

Because all the GAG chains except hyaluronic acid are heavily sulfated, the 6-sulfate inhibitors would mimic the molecular size and charge distribution of the mostly sulfated GAG chain substrates better than 6-OH compounds and thus should show better inhibition activity against hexoaminidases and consequentially the degradation of the GAG side chains. Accordingly, the 6-sulfate, 6-sulfate methyl ester 5-membered iminocyclitols 207, 212 and 215 were also synthesized and assayed for bioactivity.

Another aspect of the invention is directed to an inhibitor of hexoaminidase or glycosidase represented by the following structure:

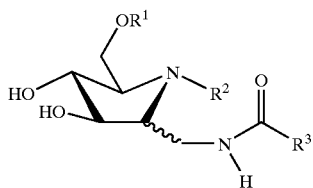

In the above structure, $R^1$ may be hydrogen, sulfate, or methyl sulfate; $R^2$ may be hydrogen, methyl, ethyl, or a branched or unbranched hydrocarbon having between 3 and 8 carbons; and $R^2$ may be a hydrocarbon having between 1 and 50 carbon atoms. In a first preferred embodiment, $R^1$ is hydrogen; $R^2$ is selected from the group consisting of hydrogen, methyl, ethyl, and a branched or unbranched hydrocarbon of between 3 and 8 carbon atoms; and $R^3$ is a hydrocarbon having between 1 and 20 carbon atoms. In an alternative to this first preferred embodiment, $R^3$ is a hydrocarbon having between 1 and 8 carbon atoms or is methyl. In a second preferred embodiment, $R^1$ is a sulfate group; $R^2$ is hydrogen methyl, ethyl or any branched or unbranched hydrocarbon of between 3 and 8 carbon atoms; $R^3$ is a hydrocarbon group that has between 1 and 20 carbon atoms. In an alternative to this second preferred embodiment, $R^3$ is a hydrocarbon group possessing between 1 and 8 carbon atoms or is methyl. In a third preferred embodiment, $R^1$ is a methyl sulfate group; $R^2$ is selected from the group consisting of hydrogen, methyl, ethyl, and a branched or unbranched hydrocarbon of between 3 and 8 carbon atoms; and $R^3$ is a hydrocarbon having between 1 and 20 carbon atoms. In an alternative to this third referred embodiment, $R^3$ is a hydrocarbon having between 1 and 8 carbon atoms or is methyl.

Another aspect of the invention is directed to an inhibitor of hexoaminidase or glycosidase represented by the following structure:

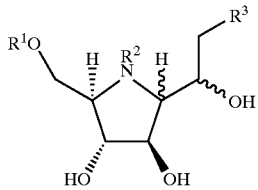

In the above structure, $R^1$ may be hydrogen, sulfate, or methyl sulfate; $R^2$ may be hydrogen, methyl, ethyl, or a branched or unbranched hydrocarbon having between 3 and 8 carbons; and $R^1$ may be hydroxyl or —NHC(O)$R^4$, wherein $R^4$ is a hydrocarbon having between 1 and 50 carbon atoms. In a first preferred embodiment, $R^1$ is hydrogen; and $R^4$ is a hydrocarbon group having between 1 and 20 carbon atoms. In an alternative to this first preferred embodiment, $R^3$ is a hydrocarbon having between 1 and 8 carbon atoms or is methyl. In a second preferred embodiment, $R^1$ is a sulfate group; $R^2$ is hydrogen, methyl, ethyl or any branched or unbranched hydrocarbon of between 3 and 8 carbon atoms; $R^3$ is a hydrocarbon group that has between 1 and 20 carbon atoms. In an alternative to this second preferred embodiment, $R^3$ is a hydrocarbon group possessing between 1 and 8 carbon atoms or is methyl. In a third preferred embodiment, $R^1$ is a methyl sulfate group; $R^2$ is selected from the group consisting of hydrogen, methyl, ethyl, and a branched or unbranched hydrocarbon of between 3 and 8 carbon atoms; and $R^3$ is a hydrocarbon having between 1 and 20 carbon atoms. In an alternative to this third referred a embodiment, $R^3$ is a hydrocarbon having between 1 and 8 carbon atoms or is methyl.

Another aspect of the invention is directed to an inhibitor of hexoaminidase or glycosidase represented by the following structure:

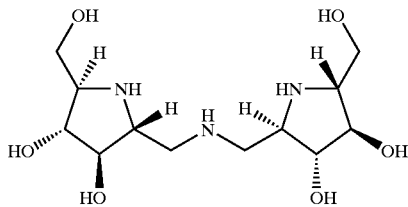

Another aspect of the invention is directed to a process for inhibiting the catalytic activity of a hexoaminidase or glycosidase comprising the step of contacting the hexoaminidase or glycosidase with any of the inhibitors indicated above with sufficient concentration for inhibiting the hexoaminidase or glycosidase.

Another aspect of the invention is directed to a process treating a subject having arthritis comprising the step of administering a quantity of any of the inhibitors indicated above to said subject sufficient for inhibiting hexoaminidase activity within said patient.

BRIEF DESCRIPTION OF DRAWINGS

FIG. 1 illustrates the proposed mechanism and transition state of β-glucosidase-catalyzed reaction and representative structures of transition-state analogue inhibitors.

FIG. 3 shows the inhibition assay results of compounds 1–9.

FIG. 13a graphs the different inhibition to MUG and MUGS with compound 107.

FIG. 13b graphs the different inhibition to MUG and MUGS with compound 108.

DETAILED DESCRIPTION

Figure 5:
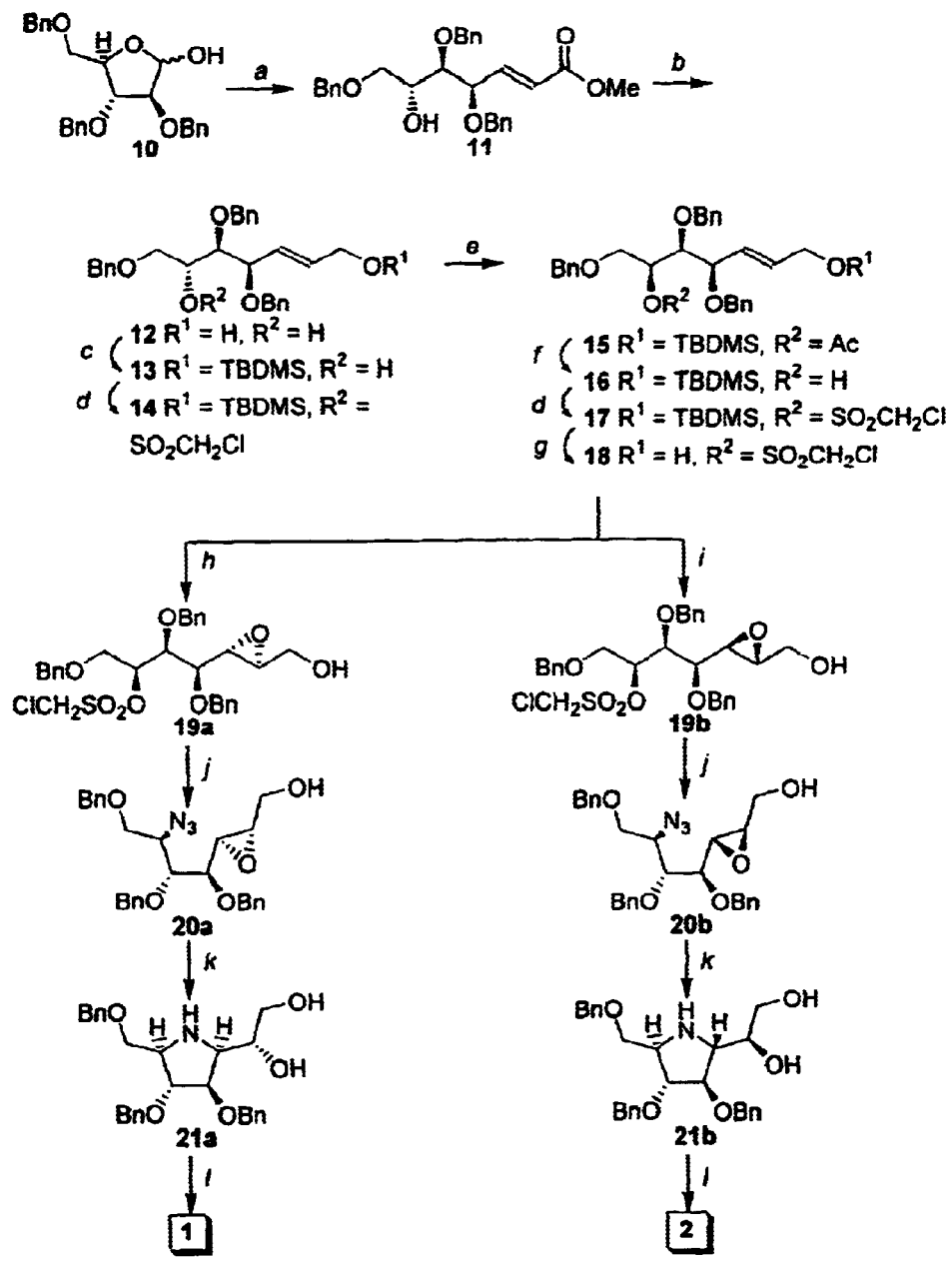
FIG. 5 illustrates the synthesis of compounds 1 and 2 from 2,3,5-benzyl-protected D-arabinofuranose (10).

Synthesis of Glycosidase Inhibitors Compounds 1 and 2:

A scheme outlining the synthesis of compounds 1 and 2 is illustrated in FIG. 5. Wittig reaction of 2,3,5-benzyl protected D-arabinofuranose (10) with methyl (triphenylphosphoranylidene)acetate afforded E-11, of which the methoxycarbonyl group was converted to the TBDMS protected alcohol (13) via di-iso-butylaluminum hydride (DIBAL) reduction followed by silylation. In order to introduce the azide function to the R-configuration at C-6 position, double inversion reactions were carried out. The 6-OH group was chloromesylated (14) and treated with CsOAc to give 15 (T. Shimizu, et al., *Tetrahedron Lett.* 1996, 37, 6145–6148). The leaving group was selected after several attempts using methanesulfonyl and trifluoromethanesulfonyl groups, which did not give satisfactory results. After removal of the acetate (16), the OH group was again chloromesylated for the second inversion (17) and the TBDMS group was deprotected to unmask the allylic alcohol for Sharpless epoxidation (18). The reason for the introduction of azide group after epoxidation is to avoid the undesired 1,3-dipole addition reaction of the introduced azide with the present double bond, which would further undergo thermolysis under the reaction conditions. The allyl alcohol 18 was epoxidized in the presence of (+)- and (−)-diethyl tartrates to afford 19a and 19b, respectively. No diastereoisomer was observed for either reaction according to $^1$H NMR. Compounds 19a and 19b were treated with NaN$_3$ to give azides 20a and 20b, both of which were subjected to a reduction condition to give 21a and 21b. Finally, benzyl groups were hydrogenolized to give the target compounds 1 and 2, respectively. Compound 2, while its configuration of C-1' was not determined, was isolated from Hyacintoides non-scripta (A. A. Watson, et al., *J. Phytochem.* 1997, 46, 255–259) and reported to have a Ki of 4 mM against β-glucosidase from Almond and a Ki of 85 mM against α-glucosidase from baker's yeast. Detailed comparison of $^1$H and $^{13}$C NMR data of these compounds revealed that they were identical. It is noted that the chloromesyl group served as a very good leaving group as well as a protecting group in these transformations.

The $^1$H NMR analysis of compounds 1 and 2 suggested that they adopted different ring conformations. The coupling constants for the ring protons of 1 were suggestive of a $^1T_2$ conformation whereas 2 was adopting the $^4T_3$ conformation (Table 1). The detailed conformations of these compounds, however, can not be discussed only by $^1$H NMR, as five member-ring compounds are known to be flexible and may exist as equilibrium mixtures (N. Asano, et al., *J. Med. Chem.* 1995, 38, 2349–2356; N. Asano, et al., *J. Nat. Prod.* 1998, 61, 625–628; and P. L. Durette, et al., *Adv. Carbohydr. Chem. Biochem.* 1971, 26, 49–125). It is assumed that 2 probably well mimics the transition state of the glycosidic cleavage.

Figure 6:
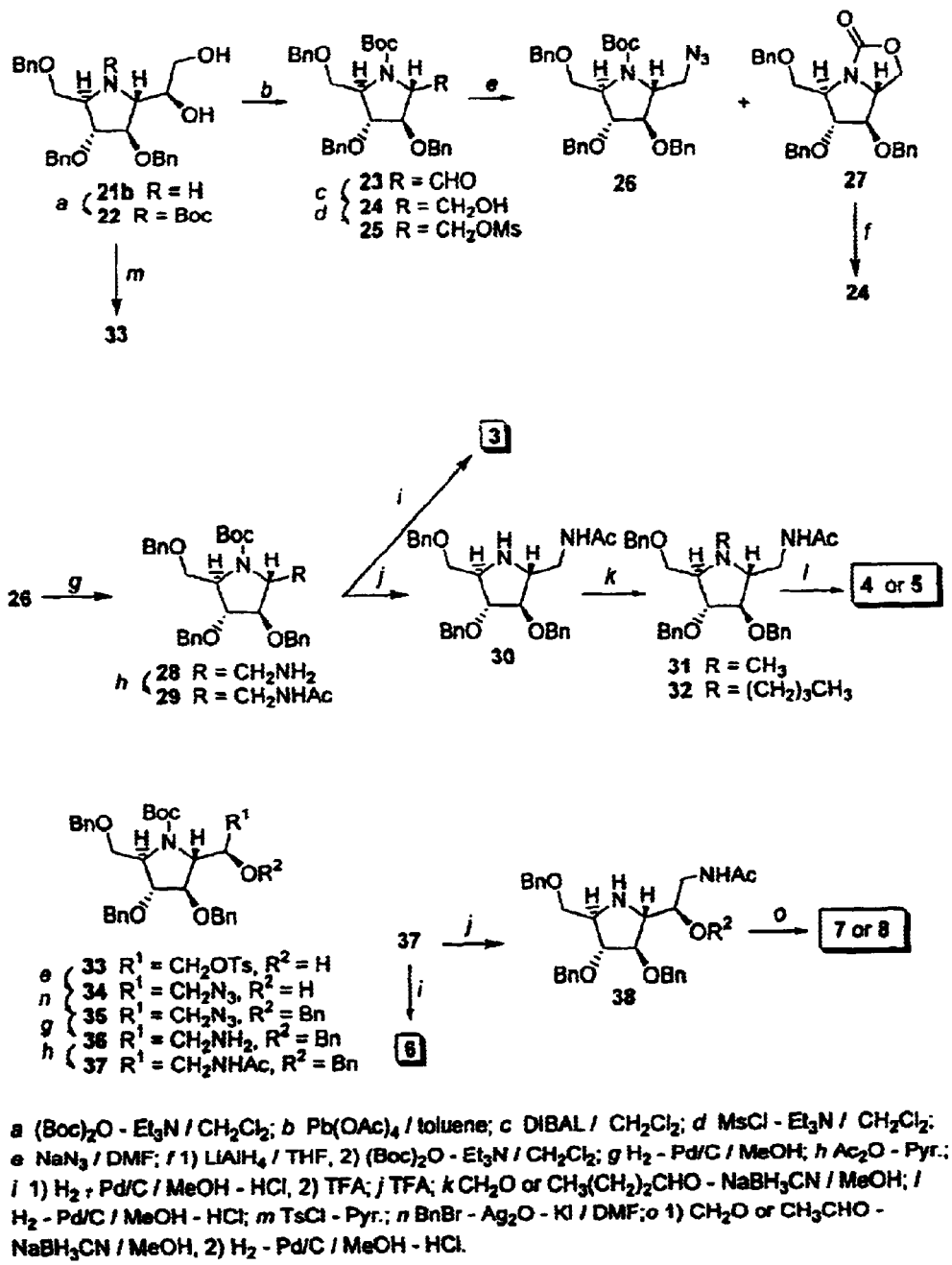
FIG. 6 illustrates the synthesis of compounds 3–8 from 21b which was obtained by the method shown in Scheme 5.
Figure 7:
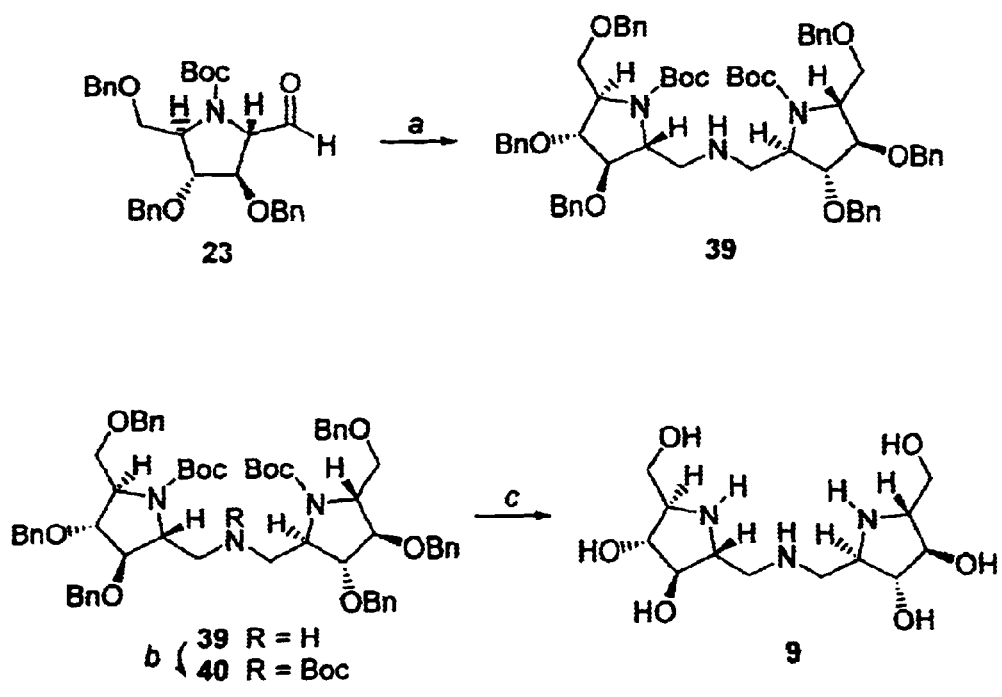
FIG. 7 illustrates the synthesis of compound 9 from compound 23.
Figure 8:
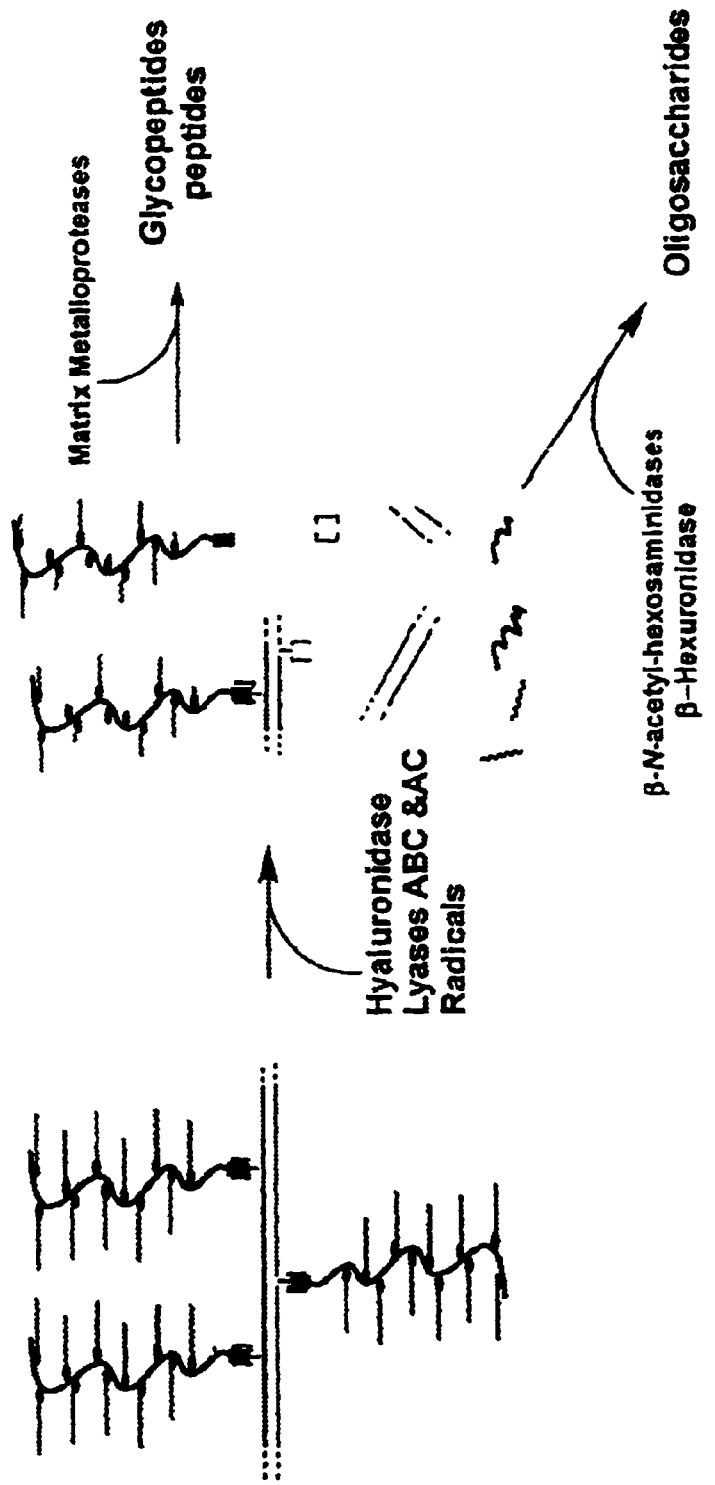
FIG. 8 is a cartoon drawing depicting the degradation of proteoglycan-hyaluronate complex.
Figure 9:
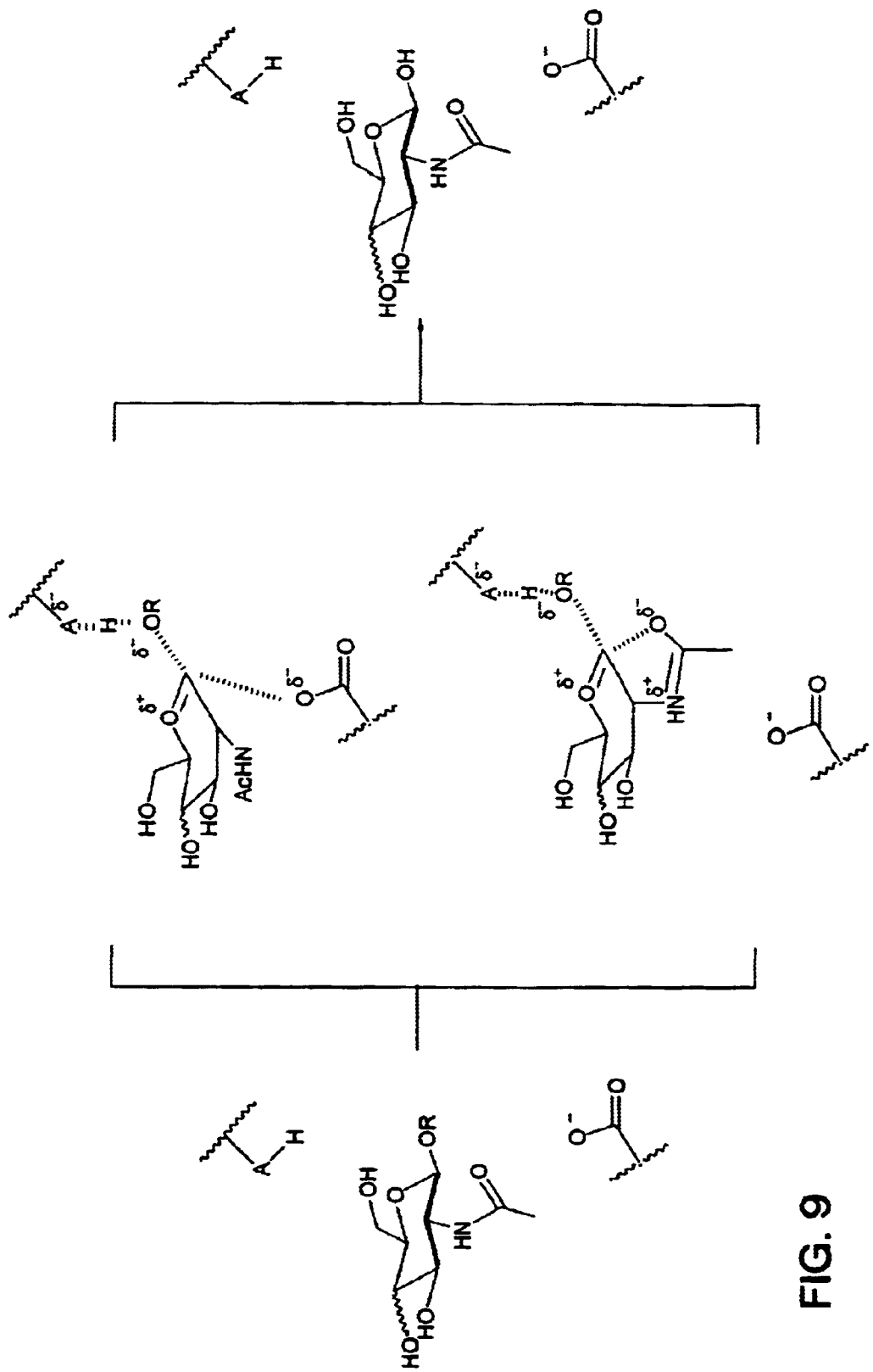
FIG. 9 displays two proposed mechanisms of N-acetyl-β-hexosaminidases.
Figure 10:
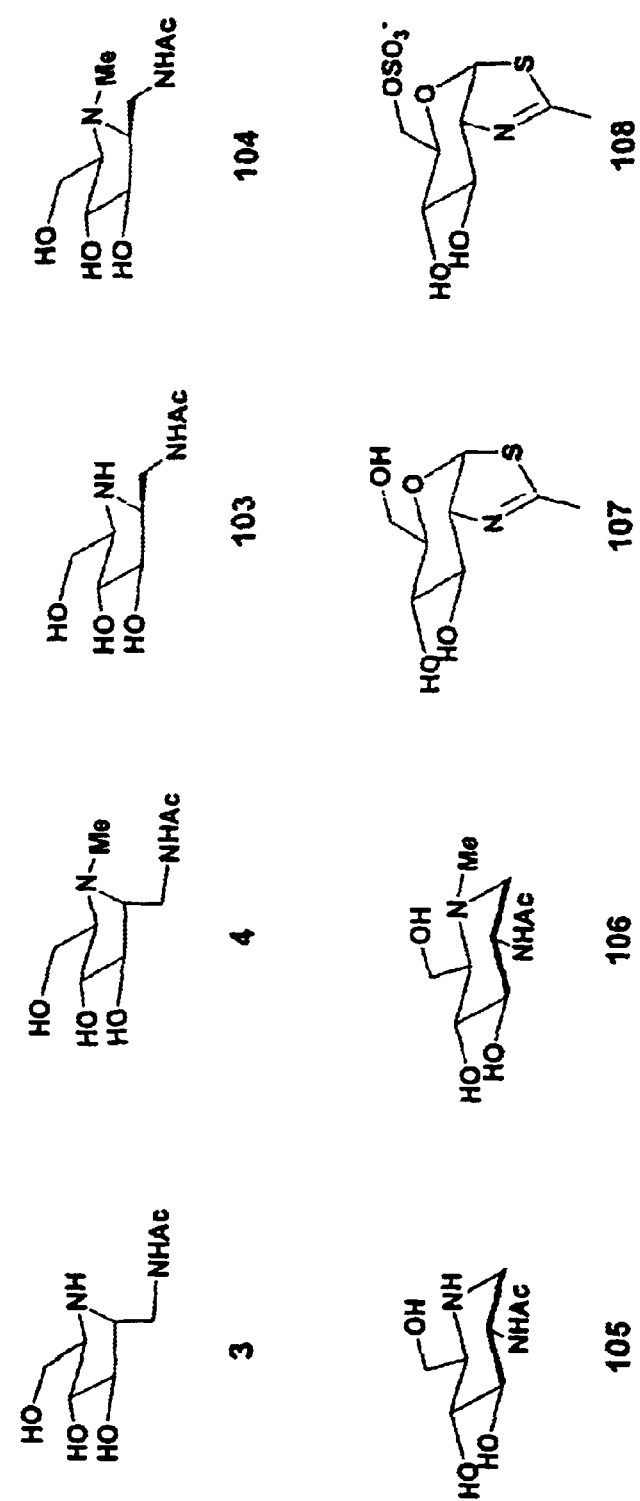
FIG. 10 shows the inhibitors of the β-N-acetylhexosaminidases that have been investigated.

Synthesis of Compounds 3–9 (FIGS. 6 and 7)

A schematic for the synthesis of compounds 3–9 is illustrated in FIGS. 6 and 7. The 2(R),5(R)-configurated structures related to 2 were selected for further characterization with the following objectives:

1) to probe the critical functional groups in inhibition;
2) to introduce functional groups to the side chain for connection to an aglycon group to create a library; and
3) to examine the potency of such compounds, including those having the NHAc group as inhibitors of β-N-acetylglucosaminidases, as 3 is known to be a potent inhibitor of the enzyme (Y. Takaoka, et al., *J. Org. Chem.* 1993, 58, 4809–4812). Synthesis of the 2(S)-isomer was also reported (M. H. Schumacher-Wandersleb, et al., *Liebigs Ann. Chem.* 1994, 555–561).

In addition to the imimocyclitol frame work with modified side chains, compounds with an alkyl group on the ring nitrogen were included because such a modification would enhance the basicity of the nitrogen atom and increase the hydrophobicity, thereby may affect the binding affinity to the target enzyme (J. Schweden, et al., *Arc. Biochem. Biophys.* 1986, 248, 335–340; G. W. Fleet, et al., *FEBS Lett.* 1988, 237, 128–132; and H. Hettkamp, et al., *Eur. J. Biochem.* 1984, 142, 85–90).

Compound 21b was used as a starting material for the syntheses of compounds 3–9. The secondary amine function of 21b was protected with the Boc group (22), of which the C-1'–C2' bond was cleaved using Pb(OAc)$_4$ to give the aldehyde 23. Compound 24 obtained by reduction of the aldehyde function using DIBAL was mesylated (25) and treated with NaN$_3$ to afford 26. During the substitution reaction, 27 was obtained as a by-product (28%), which could be converted back to 24. The azide group was then reduced selectively in the presence of benzyl groups and the amine was acetylated to give 29. Protecting groups were finally removed sequentially by hydrogenolysis and acid hydrolysis to give compound 3. When the Boc group was removed first followed by hydrogenolysis, the process took a longer reaction time (1 week) and gave a mixture of 3 and 4.

In order to obtain compounds 4 and 5, the Boc group of 29 was deprotected (30) followed by N-methylation via reductive alkylation, and the benzyl groups were hydrogenolized to give 4 or 5.

The intermediate 22 was also utilized to obtain 6–8. Compound 22 was converted to the 2'-acetamido compound (37) via tosylation (33), substitution reaction with NaN$_3$ (34), benzylation (35), and selective reduction of the azide function to an amine followed by acetylation (37). Sequential deprotection of the benzyl group and the Boc group resulted in 6.

Compound 37 was treated with TFA to give 38 which was alkylated in the same manner as for the syntheses of 4 and 5 and finally hydrogenolized to afford 7 and 8. The dimer 9 was obtained as the result of self-quenching under reductive amination in the presence of ammonium acetate followed by deprotection.

Figure 14:
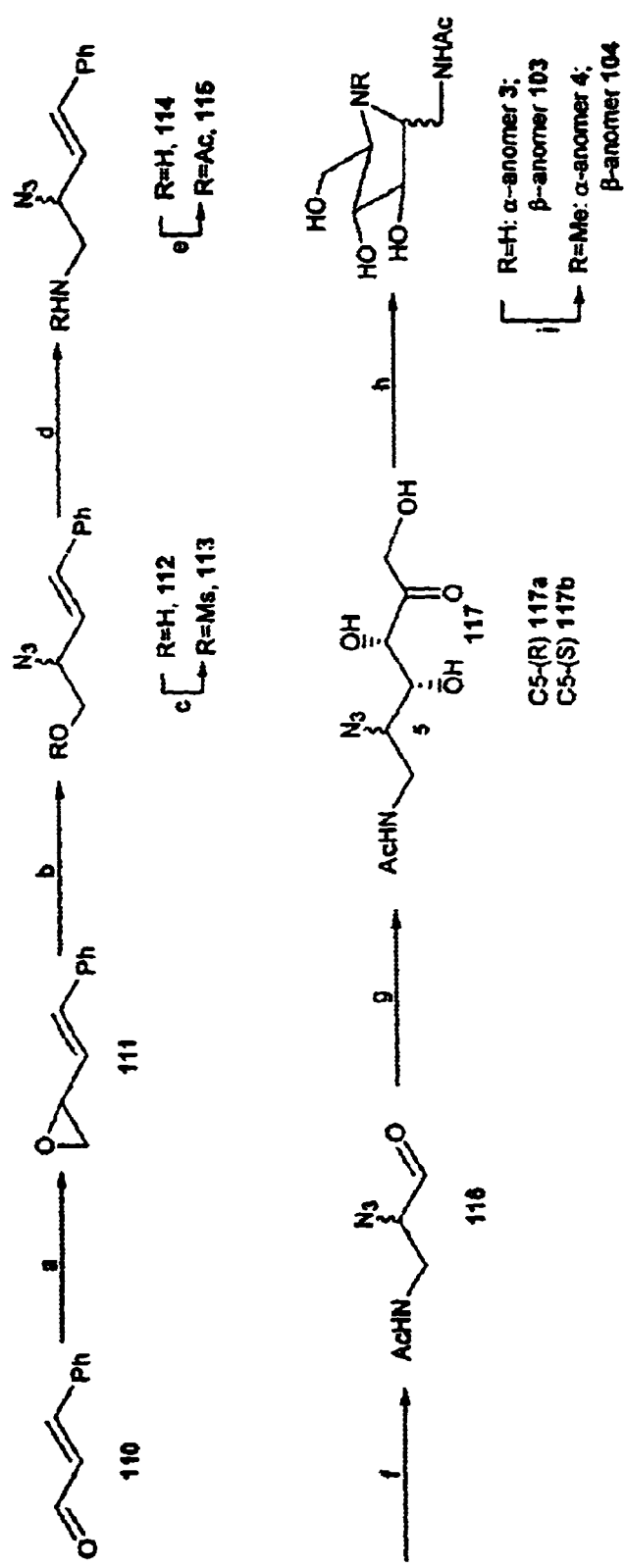
FIG. 14 illustrates the scheme used to make compounds 3, 4, 103 and 104.

Synthesis of Hexoaminidase Inhibitors
Synthesis of Five-membered Acetamido-iminocyclitols:

Iminocyclitols were prepared through the condensation of an aldehyde with dihydroxyacetone phosphate (DHAP) (C.-H. Wong. et al., *Angew. Chem. Int. Ed. Eng.* 1995, 34, 412; and H. J. M. Gijsen, et al., *Chem. Rev.* 1996, 96, 443). Both α and β five-membered acetamido-iminocyclitols and their derivatives were prepared following the procedures outlined in FIG. 14 according to the method of Takaoka et al. (Y. Takaoka, et al., *J. Org. Chem.* 1993, 58, 4809).

Trans-cinnamaldehyde was first reacted with dimethyl-sulfonium methylide, which was prepared in situ, to get the epoxy-phenyl butene 109. Treating with $NaN_3$ in acetone/water, we got the racemic hydroxyamine 110. Mesylation of the compound 110 afforded compound 111, which was treated with hexomethylene tetramine to yield the ammonium salt. Without purification, the crude product was converted to the primary amine 112 by the hydrolysis with concentrated HCl.

Since both α and β isomers were needed by us, no resolution step was conducted. Without purification, the amine compound 112 was acetylated with isopropenyl acetate to afford a racemic mixture 113.

Ozonolysis of the mixture in methanol under −78° C., followed by worked up with dimethyl sulfide produced the racemic aldehydes 114. The mixture was directly condensed with DHAP, catalyzed by FDP-aldolase. The phosphate group of the aldol products was removed by acid phosphatase to yield 115a and 115b, which can be efficiently separated by the silica gel chromatography. Stereoselective hydrogenation afforded compound 3 and 4.

The two five-membered iminocyclitols 3 and 4 were hydrogenated with formaldehyde in methanol/water. The N-methyl derivatives 103 and 104 were prepared respectively in high yield.

The N-methyl-β-isomer iminocyclitol 104 can also be prepared from 2,5-anhydro-2,5-imino-D-Glucitol 116 which can be produced in large quantities by the microbial oxidation of fructose (E. W. Baxter, et al., *J. Org. Chem.* 1994, 59, 3175). Further straightforward manipulation afforded the key intermediate 117 (C.-H. Wong, et al., *J. Org. Chem.* 1995, 60, 1492).

Figure 15:
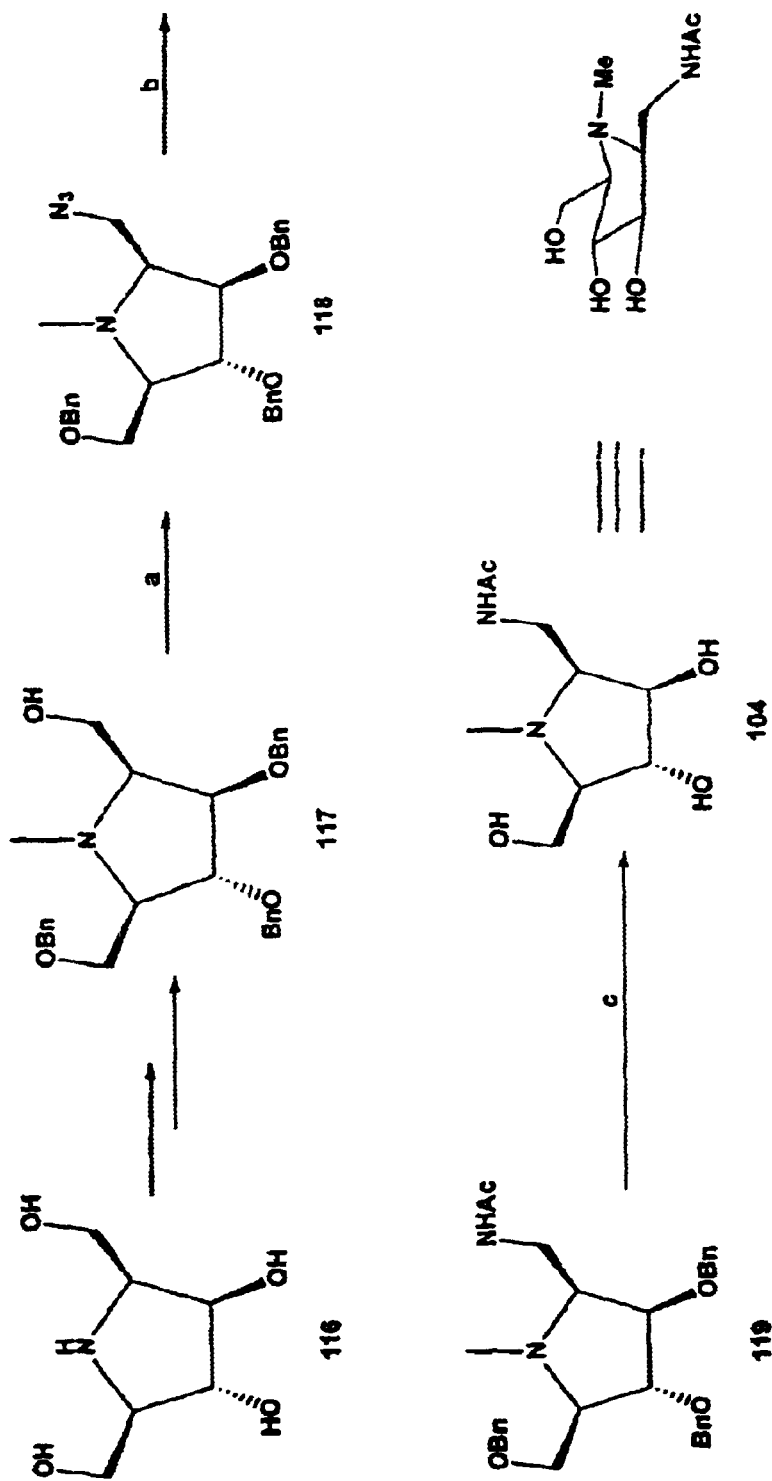
FIG. 15 illustrates a second scheme used to make the 5-membered β-acetamido iminocyclitol 104.

As illustrated in FIG. 15, after activation the hydroxyl group in 117 with MsCl, the crude product was directly treated with $NaN_3$ in pyridine to afford azide compound 118. After reduction of the azide and acetylation of the amine, the tribenzyl-protected five membered ring iminocyclitol's β-isomer 119 was yielded. The final N-methyl-β-acetamino-iminocyclitol 104 was prepared in high yield after complete hydrogenation.

Figure 16:
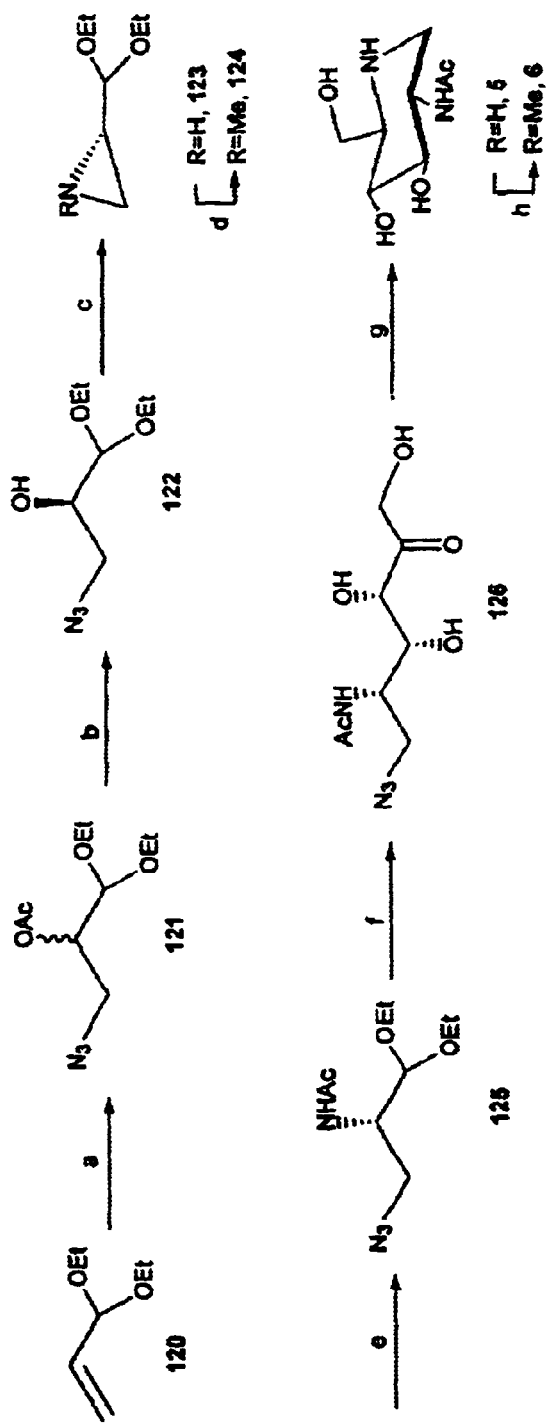
FIG. 16 illustrates the scheme used to synthesize the 6-membered 2-acetamido-iminocyclitols 105 and 106.

Synthesis of Six-membered 2-Aceamido-2-deoxy-iminocyclitols:

The synthesis of the six membered ring iminocyclitols was achieved according to the method of T. Kajimoto, et al. (T. Kajimoto, et al., *J. Am. Chem. Soc.* 1991, 113, 6187) and as outlined in FIG. 16. Starting from the commercial available compound 120, the azide compound 121 was synthesized in a one-pot reaction. Through the resolution with the lipase PS-80, the desired enantiomer was selectively deacetylated to afford alcohol 122. Under the classical condition, the aziridine 123 was prepared. Acetylation afforded 124. Nucleophilic opening of the aziridine with sodium azide in the presence of $ZnCl_2$ gave 125 in 62% yield. After acid hydrolysis to unmask the aldehyde protecting group, the aldehyde product of compound 125 was condensed with DHAP in the presence of FDP aldolase. The phosphate group of the aldol product was then removed by acid phospatase to yield 126 as before. 126 was converted to iminocyclitol 105 via reductive amination. Following the same procedure described in the preparation of the five-membered ring iminocyclitols, N-methyl product 106 can also be prepared.

Synthesis of N-Acetylhexosamine-thiazoline

Figure 17:
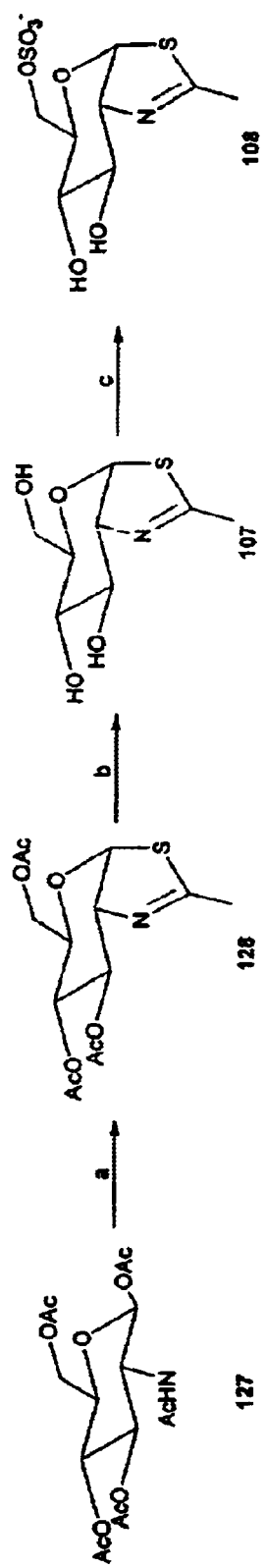
FIG. 17 shows the synthesis of NAG-thiazoline (108) from the starting 2-acetamido-iminocyclitol 127.

Following the procedure suggested by Knapp S. et al. (S. Knapp, et al., *J. Am. Chem. Soc.* 1996, 119, 6804), the target compound was synthesized according to the method outlined in as FIG. 17.

Figure 18:
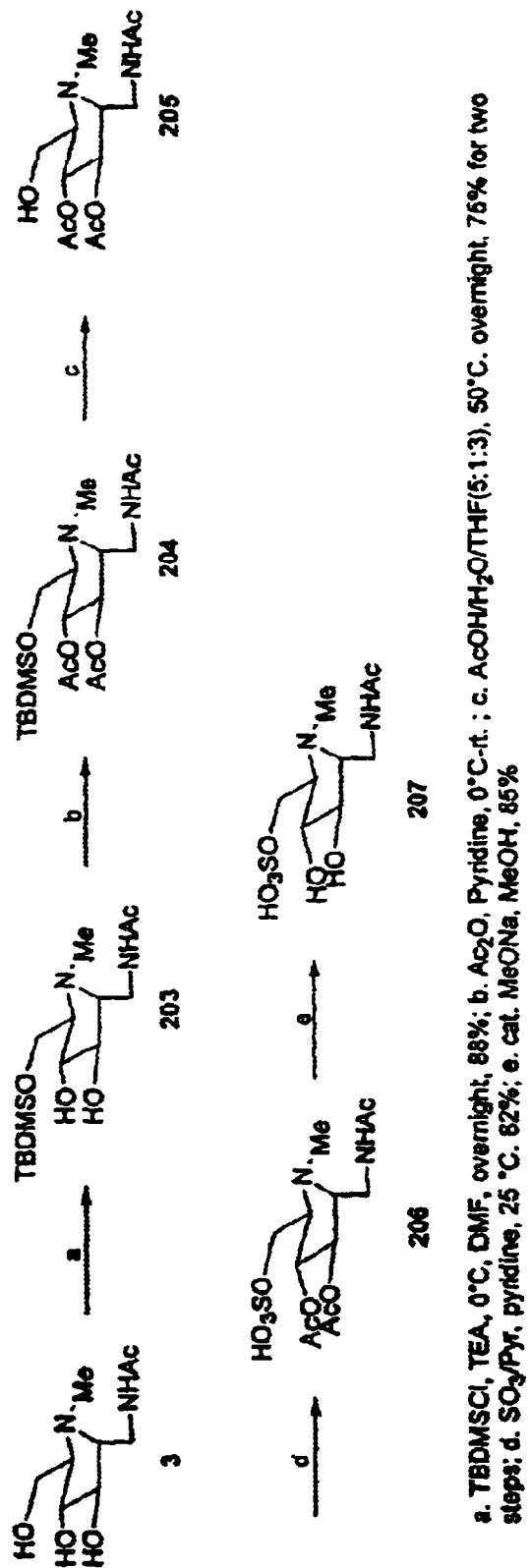
FIG. 18 depicts the steps taken to synthesize the sulfated iminocyclitol 207 starting from compound 3.

The preparation of the 6-sulfated α-iminocyclitol 207 starts from the its parent compound 3 according to the method outlined in FIG. 18.

The primary hydroxyl group in 3 was first selectively protected with TBDMSCl; TBDMSOTf was found to afford a mixture of primary and secondary silyl ethers. The remaining two secondary OH groups in 203 were then protected as acetates to give the fully protected α-iminocyclitol 204. Under acidic condition, the silyl ether was cleaved to afford 6-OH α-iminocyclitol 205 in a yield of 75% for two steps. Treating 205 with $SO_3$(pyridine complex in pyridine provided the diacetyl protected sulfated α-iminocyclitol 206 in 82% yield. Removal of the two acetate produced the target sulfated α-iminocyclitol 207 in a yield of 85%.

Figure 19:
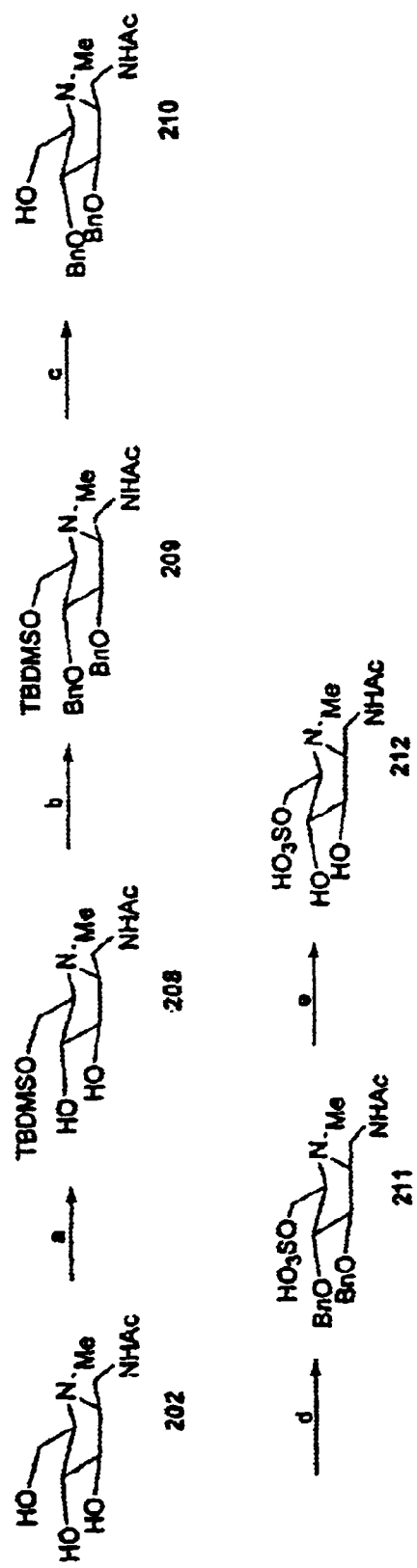
FIG. 19 depicts the steps taken to synthesize the sulfated iminocyclitol 212 starting from compound 202.

The sulfation of β-iminocyclitol 202 was provided different results (FIG. 19). The hydroxies in the β-iminocyclitol 202 seemed much less active than those in α-iminocyclitol 3. The 6-OH doesn't react with TBDMSCl even at elevated temperatures (130° C.). However, the primary hydroxyl group of 202 reacted exclusively with TBDMSOTf at 0° C. to afford 6-silyl ether protected iminocyclitol 208 in 90% yield. The different reactivities between 3 and 202 can be explained by the steric effect. There is more steric hindrance in the β-iminocyclitol 202 than in 3 due to the extending direction of N-acetyl group. The steric hindrance is enhanced by the smaller nitrogen atom relative to the oxygen which make the iminocyclitols very compact.

The silyl ether in 209 was cleaved with TBAF in THF to afford 6-OH compound 210 in 80% yield. Treating 210 with $SO_3$(pyridine complex in pyridine provided the benzyl protected sulfated iminocyclitol 211 in 80% yield. Hydrogenation with $Pd(OH)_2/C$ afforded the sulfated β-iminocyclitol 212 in a yield of 75%.

Figure 20:
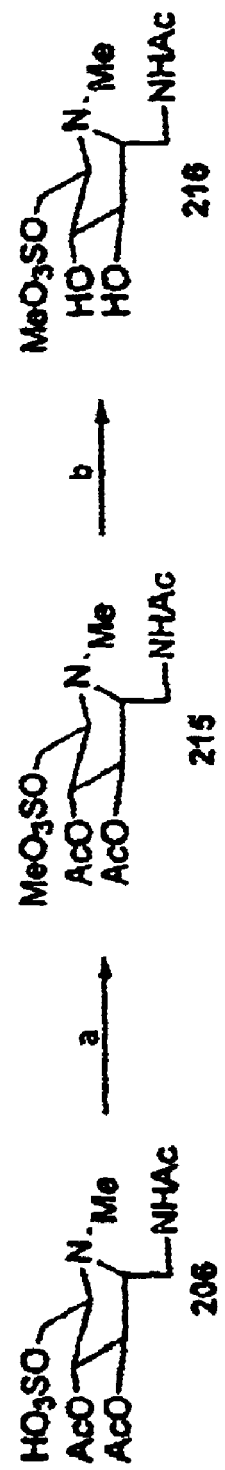
FIG. 20 illustrates the two step synthesis of the sulfate methyl ester iminocyclitol 216 from compound 206.

In the whole cell assay, the Ki's of both inhibitors 207 & 212 were in mM scale. Obviously, The negative charge of the sulfated iminocyclitols 207 and 212 made it difficult for them to reach and penetrate the cell. To deal with this problem, we employed a prodrug approach: changing the sulfated iminocyclitols to their methyl esters may allow their transportation into the cells. We hypothesized that the sulfate methyl esters can be hydrolyzed to 6-sulfate iminocyclitols at the target positions and then the 6-sulfate compounds can show their inhibition activity. Based on the prodrug approach, the sulfate methyl esters should be potent inhibitors against hexoaminidases in vivo. The synthesis of 6-sulfate methyl ester of α-iminocyclitols was described in FIG. 20.

The 6-sulfate protected iminocyclitol 206 was methylated in methanol at 50° C. in one hour. The subsequent deprotection with catalytic MeONa gave the 6-sulfate methyl ester α-iminocyclitol 216 in 80%.

The bioassay results confirmed the activity of these compounds. The Ki of the 6-sulfate methyl ester α-iminocyclitol 216 was 20 nM in the whole cell assay. We also found that 216 could selectively inhibit hexoaminidase A without inhibition of hexoaminidase B. Because HexA accepted both sulfated and non-sulfated substrates while HexB only accepted non-sulfated substrates, the selective inhibitors to HexA may have less side effect on the metabolism of nonsulfated glycans while they delayed the degradation of GAG side chains, which are heavily sulfated.

Figure 2:
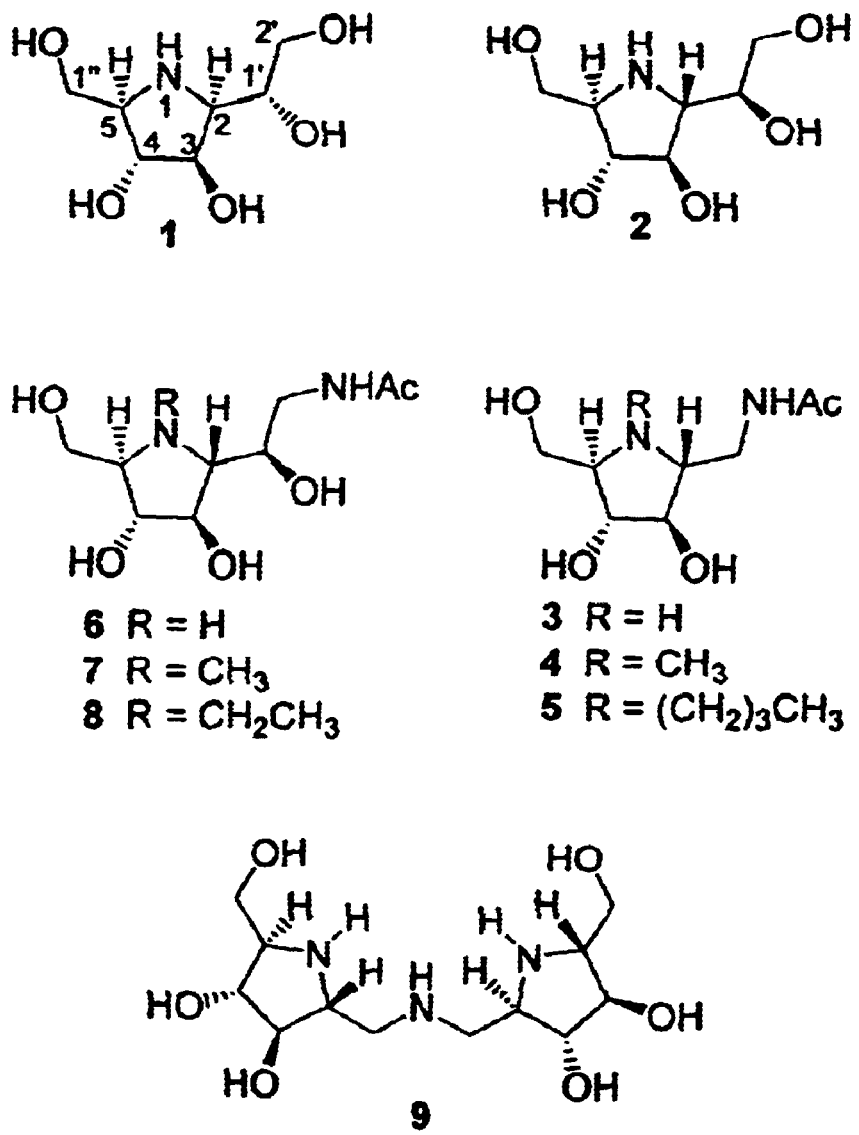
FIG. 2 shows the iminocyclitol structures.
Figure 4:
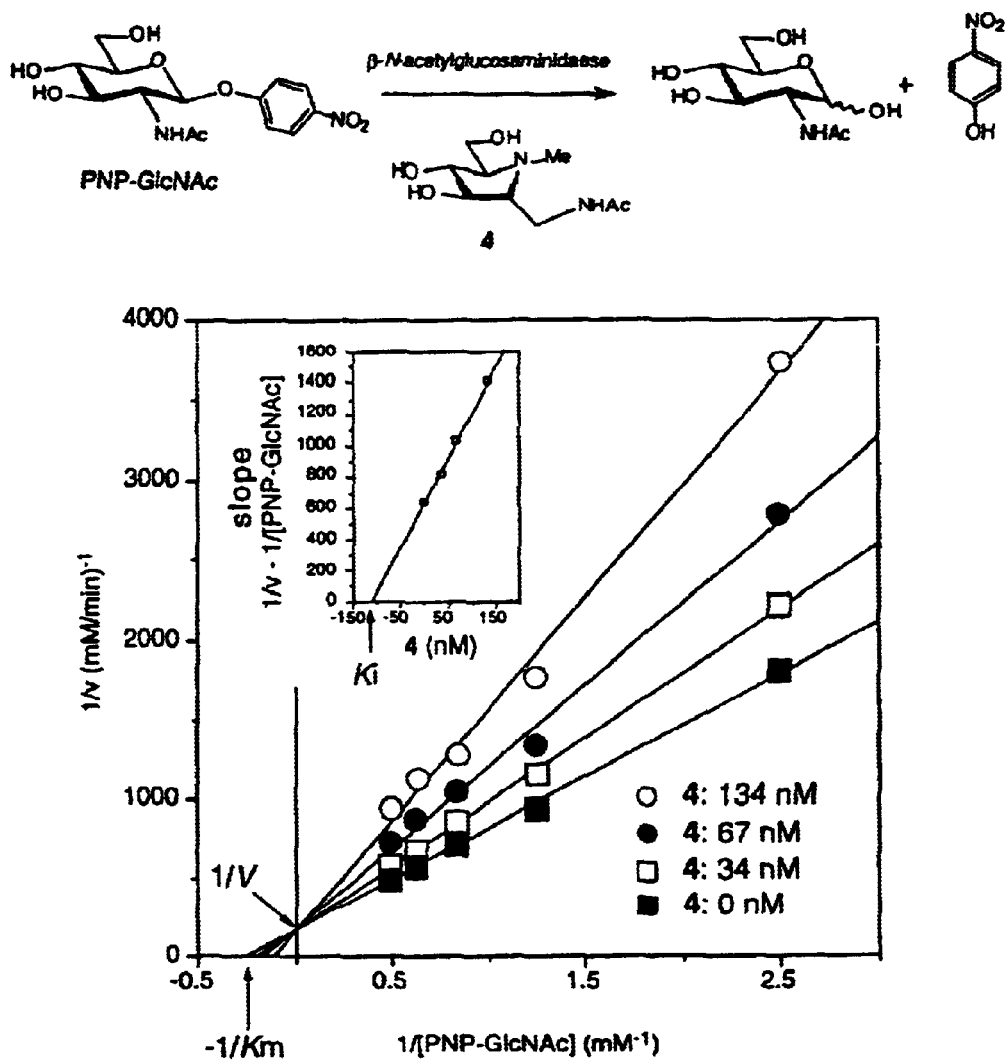
FIG. 4 shows the double reciprocal plots carried out to obtain $K_m$ and $V_{max}$ values. Also $K_i$ values were obtained from a replot of the slopes obtained from the double-reciprocal plot. As representative of such plots, a double-reciprocal plot of 1/v vs 1/[S] in the β-N-acetylglucosaminidase reaction was shown. The concentrations of 4 were (■) 0 nM, (□) 34 nM, (●) 67 nM, and (○) 134 nM. The $K_m$ value calculated from the plot (■) was 4.1 mM, (Inset) Replot of slopes {[1/(v−1)]/[PNP-GlcNAc]} vs 4. $K_i$ for 4=0.11 µM.

Inhibition Analysis of Glycosidase Inhibition Activity With CZE (FIG. 4)

A conventional method for the assay of glycosidase reactions is based on spectrophotometric analysis using chromogenic aglycons to detect the released chromophore directly (J. Borooah, et al., *Biochem. J.* 1961, 78, 106–110; D. Leaback, et al., *Biochem. J.* 1961, 78, 151–156; and R. G. Price, et al., *Biochem. Biophys. Acta* 1972, 271, 145–153) or using a substrate so the product is detected with an NADH coupled reaction (D. K. Fitzgerald, et al., *Anal. Biochem.* 1970, 36, 43–61). As an alternative to radioactive analytical methods, CZE may be employed, as indicated supra. The CZE technique was herein employed as a general analytical method not only for glycosyltransferases but also for glycosidases. In addition, since the method relies on the peak separation, potential ambiguity arising from the possibilities of formation of byproducts can be eliminated. The analysis of transferase reactions requires peak separation of the substrate and the product before the actual kinetic analysis; however, the analysis of glycosidase reactions was more straightforward because the cleaved chromophore is usually acidic and can easily be distinguished from neutral carbohydrates. To make the CZE analysis a general method, however, a condition must be identified (usually the buffer system) that gives different migration times for the substrate and the released aglycon. This is especially necessary in the case where the released aglycon does not have a specific absorbance or fluorescence.

Initially, the total volume of assay solution was reduced because this is the only way to reduce the amount of enzyme and substrate used in the assay. The 96-well microtiter plate with a round bottom was used for the assay, and each well was sealed with tape. Thus, the assay was examined and carried out in a total volume of as little as 20 μL containing 1.76 mU of a glycosidase such as β-N-acetylhexosaminidase P. The electrophoresis was carried out using 50 mM borate buffer (pH 9.2~10.2) as the electrolyte and the progress was monitored at 37° C. The injected volume of approximately 38.4 nL of a reaction mixture contained as little as 3.8 pmol of the substrate p-nitrophenyl (PNP) glycoside, thus the amount of PNP detected was less than $10^{-12}$ mol. The peak corresponding to the p-nitrophenol, which appeared at around 6.5 min. in these conditions, was monitored at 405 nm.

The inhibition studies of compounds 1–9 against α- and β-glucosidases (front Saccharomyces sp. and sweet almond, respectively) were carried out. PNP-glycosides of the parent sugars were used as the substrates throughout the assay. The apparent $K_m$ and $V_{max}$ values for each substrate were calculated from the double-reciplocal plot of standard 1/v– 1/[substrate] curve.[18] The $K_i$ values were determined from a replot of the slopes of Lineweaver-Burk plots vs. the inhibitor concentrations. The analysis of inhibition of β-N-acetylglucosaminidase from bovine kidney by 4 was shown in FIG. 4, where the apparent $K_m$ and $V_{max}$ values for PNP-GlcNAc were determined to be 4.1 mM and 6.4 μM/sec/mg, and the Ki value of the competitive inhibitor 4 was determined to be 0.11 μM. Kinetic parmeters thus obtained for the enzymes examined with other inhibitors were shown in FIG. 4.

As shown in FIG. 3, remarkable inhibitory specificities were observed for the compounds synthesized against glycosidases. Compounds 1 and 2 were designed and synthesized previously to inhibit β- and α-glucosidase, respectively. In our design, the side chain at position 2 in each compound is modified to mimic the aglycon part of the substrate for each enzyme. However, compound 2 showed potent inhibitory activities against both α- and β-glucosidases, whereas 1 was shown to be a weak inhibitor against both enzymes. Previously, inhibition assays of aza-sugars 1 and 2 using photometric assay system were carried out, which showed good agreement to the results obtained by CZE. The differences in the inhibitory activities may be explained by their conformational differences as suggested by the $^1$H NMR analysis (Table 1). The N-methylated derivatives of 1 and 2 were also prepared, but exhibited weaker inhibitory activities against both enzymes ($IC_{50}$>1 mM).

Replacement of the 2'-hydroxyl group of 6 with the NHAc group had no impact on the activity towards glucosidases. It showed an identical inhibitory activity to 2, but alkylation of the ring nitrogen had negative effects.

Compounds 3–5, which lack one carbon and one hydroxyl group, showed no inhibitory activity against β-glucosidase up to 500 μM and only very weak inhibition against α-glucosidase. Instead, these compounds were found extremely potent inhibitors of N-acetylglucosaminidase from bovine kidney (Y. Takaoka, et al., *J. Org. Chem.* 1993, 58, 4809–4812) and human placenta (A and P). Also, methylation of the ring nitrogen improved the activity; however, a decrease in activity was observed with a longer N-alkyl substituent.

It was revealed that an acetamido group is necessary at the C-1' position of the five membered iminocyclitols in order to inhibit N-acetylglucosaminidase. It was also revealed that, in the case of inhibition of glucosidases, a OH group at C-1' is required, perhaps to mimic the OH-2 group of glucose. The dimeric derivative 9, however, has an inhibitory activity at the same level as 1 and 7 toward the β-glucosidase, and also is as effective as 2 toward the α-glucosidase despite the absence of an OH group to mimic the OH-2 group of glucose. The additional moieties may have used to circumvent the lack of OH group or to give additional binding affinity (E. A. MacGregor, et al., *Biochem. J.* 1989, 259, 145–152).

Figure 11:
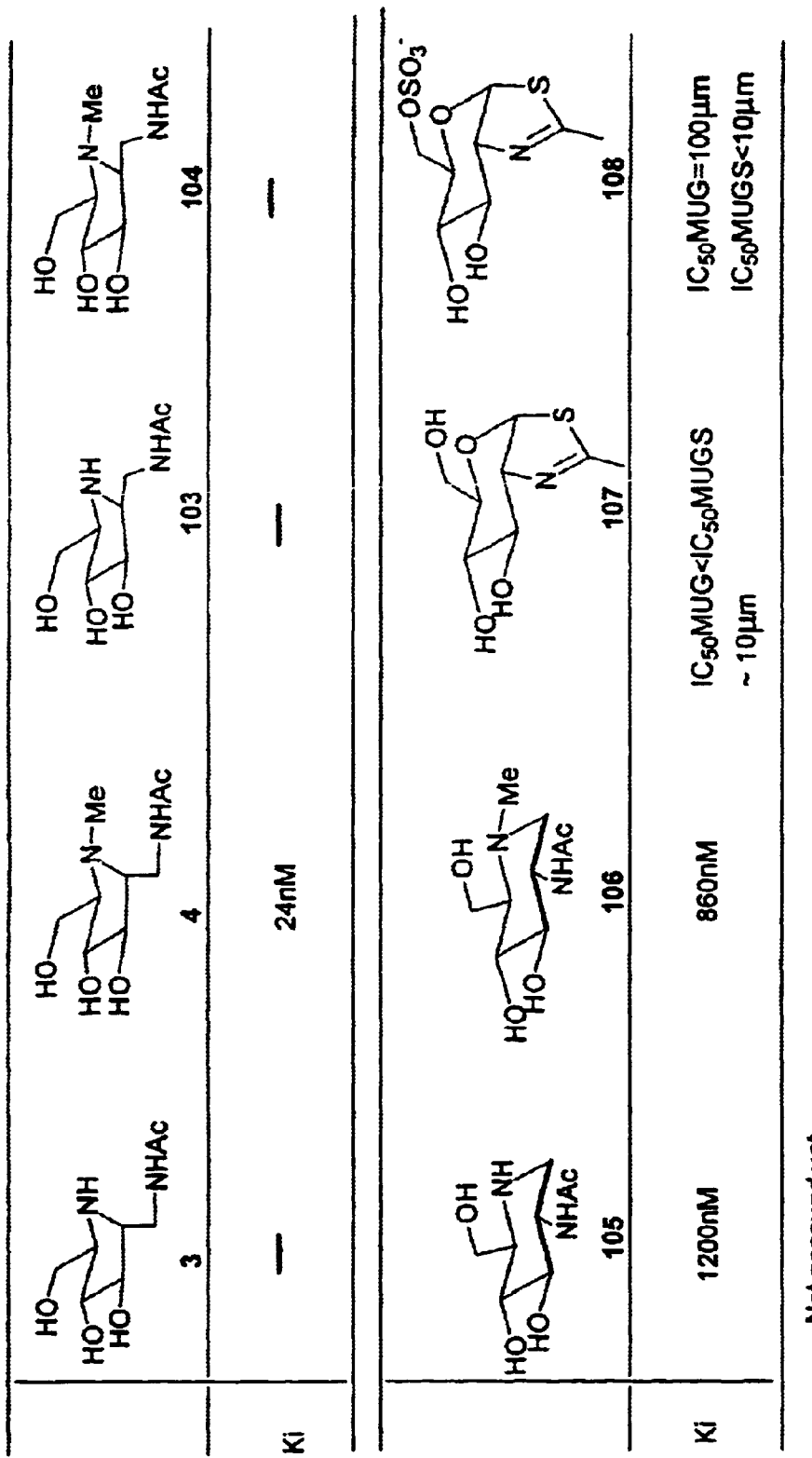
FIG. 11 lists the inhibition activities of the synthesized compounds when tested with NAG-HexA.

Inhibition Assay for Hexoaminidases:

The indicated compounds synthesized above have been assayed and found to be potent inhibitors of β-N-acetylhexaoaminidases A from human placenta (FIG. 11), especially the 5-membered iminocyclitol compound 4(Ki= 24 nM). The potent inhibition can be explained by virtue of the ring nitrogen, protonated at the physiological pH, mimicking the positive charge of the oxonium ion. In addition, the transition state conformation is mimicked better by the five member ring here. The participation of 2-acetamido group is less important in this case.

Figure 12:
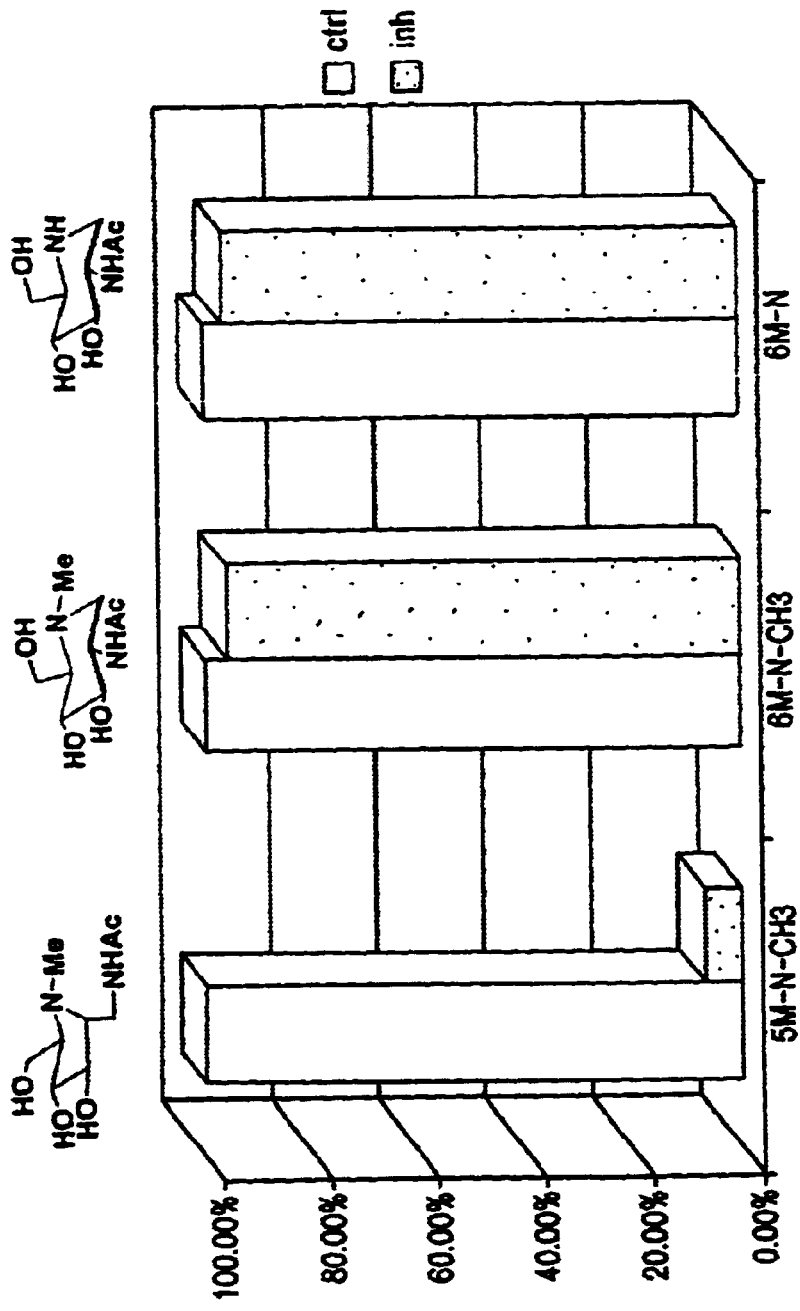
FIG. 12 shows a bar graph comparing the intracellular effects of different inhibitors.

The most exciting result is shown in FIG. 12, the intracellular β-N-acetylhexaoaminidases activity is dramatically decreased by inhibitor 4 in contrast to the six-membered iminocyclitols 105 and 106. That suggests that the five-membered iminocyclitol 4 can penetrate through the cell membrane and inhibit the β-N-acetylhexoaminidases in the cytoplasm. The whole cell assay shows that compound 4 can decrease the GAGs' extracellular concentration and increase GAG's intracellular concentration.

When the β-N-acetylhexosaminidase A was used, the sulfated thiazoline 108 was found to show higher inhibition activity towards the 6-sulfate-4-methyl-umbelliferyl-β-D-N-acetylglucosamine (MUGS) than to 4-methyl-umbelliferyl-β-D-N-acetylglucosamine (MUG). In contrast, 107 shows higher inhibition activity to MUG than to MUGS as illustrated in FIGS. 13A and 13B.

All the GAG chains except hyaluronic acid are sulfated (T. T. Giant, et al., *J. Immunol.* 1998, 28, 3812). This result implies, as a general rule, that sulfated inhibitors maybe show better inhibition activity than the nonsulfated ones for the GAG side chains.

Experimental
General Methods for the Synthesis

Dried solvents were used for all reactions. Solutions were evaporated under reduced pressure at a bath temperature not exceeding 50° C. Column chromatography was performed on silica gel or Iatro Beads (60μ). Gel permeation chromatography was performed using Bio Gel P-2. Melting points were measured with a melting point apparatus and are uncorrected. Optical rotations were measured in a 1.0 dm tube with a polarimeter at 24±1° C. $^1$H NMR (270 MHz) were recorded on solutions in $CDCl_3$ or $D_2O$ using $Me_4Si$ (δ 0.00) or DOH (δ 4.80) as the internal standard. $^{13}$C NMR (67.5 MHz) spectra were recorded on solutions in $CDCl_3$ or $D_2O$ using $Me_4Si$ (δ 0.00), $CDCl_3$ (77.00), $CD_3CN$ (δ 118.20), or $CD_3OD$ (δ 49.80) as the internal standard. Some key compounds were measured with a 400 MHz spectrometer as indicated. Only partial assignments were reported. The FAB mass and HR FAB mass spectra were obtained with glycerol and 3-nitrobenzylalcohol as the matrix. MALDITOF mass spectra were recorded with 2,5-hydroxybenzoic acid as the matrix.

Methyl (4R,5R,6R)-6-hydroxy-4,5,7-tribenzyloxy-2(E)-heptenoate (11): A solution of 2,3,5-tri-O-benzylarabinofuranose (10) (420 mg, 1.0 mmol) and methyl (triphenylphosphoranylidene)acetate (435 mg, 1.3 mmol) in benzene (10 mL) was heated under reflux for 12 h. After cooling, the solvent was removed in vacuo and the crude mixture was purified by flash column chromatography (3:1 hexane-EtOAc). The E-isomer (11) was obtained as a major product (419 mg, 88%), $[α]_D$ −4.1° (c 2.2, $CHCl_3$) along with the Z-isomer (47 mg, 10%).

(4R,5R,6R)-4,5,7-tribenzyloxy-2(E)-hepten-1,6-diol (12): To a solution of compound 11 (3.9 g, 8.19 mmol) in dry $CH_2Cl_2$ was added 1 M solution of DIBAL (24.6 mL, 3 eq) at 0° C. The reaction mixture was stirred at the temperature for 1.5 h. MeOH (4 mL) was added at 0° C. and the temperature was raised to r.t. Sat. NaCl (8 mL) was added and the mixture was diluted with $Et_2O$ (200 mL). $MgSO_4$ (21 g) was added and the whole mixture was stirred for 1 h, then filtered through Celite pad. The solvent was removed in vacuo and the crude mixture was purified by column chromatography (1:1 hexane-EtOAc) to give the alcohol 12 (3.54 g, 96.5%). $[α]_D$ −22.6° (c 1.0, $CHCl_3$).

(4R,5R,6R)-1-tert-butyldimethysilyloxy-4,5,7-tribenzyloxy-2(E)-hepten-6-ol (13): Compound 12 (5.17 g, 11.54 mmol) was dissolved in DMF (100 mL), to this solution was added TBDMSCl (2.09 g, 13.9 mmol), $Et_3N$ (4 mL, 28.85 mmol) and DMAP (50 mg). The reaction mixture was stirred at r.t. for 1 h. The mixture was diluted with EtOAc and the organic layer was washed with $H_2O$, brine and dried with $Na_2SO_4$. After removal of the solvent, the residue was purified by column chromatography (10:1 hexane-EtOAc) to give 13 (6.15 g, 95%) as a colorless oil, $[α]_D$ −18.2° (c 1.05, $CHCl_3$).

(4R,5R,6R)-1-tert-butyldimethylsilyloxy-6-[(chloromethylsulfonyl)-oxy]-4,5,7-tribenzyoxy-2(E)-heptene (14): A solution of compound 13 (480 mg, 0.85 mmol) and chloromethylsulfonyl chloride (91 mL, 1.0 mmol) in pyridine (2 mL) was stirred at r.t. for 0.5 h, then the mixture was diluted with EtOAc and washed with $H_2O$ and brine, and dried over $Mg_2SO_4$. After removal of the solvent, the residue was purified by column chromatography (10:1 hexane-EtOAc) to give 14 (564 mg, 98%) as a colorless oil.

(4R,5R,6S)-6-acetoxy-1-tert-butyldimethylsilyloxy-4,5,7-tribenzyl-oxy-2(E)-heptene (15): The stirred mixture of compound 14 (2.40 g, 3.56 mmol), CsOAc (3.40 g, 5 eq), and 18-crown-6 (950 mg, 1 eq) was heated under reflux in toluene (80 mL) for 12 h. After cooling to r.t., the reaction mixture was washed with $H_2O$ and brine, dried over $Na_2SO_4$, and the solvent was removed in vacuo. The crude material was purified by column chromatography (10:1 hexane-EtOAc) to afford 15 (1.98 g, 92%) as a colorless oil.

(4R,5R,6S)-1-tert-butyldimethylsilyoxy-4,5,7-tribenzyloxy-2(E)-hepten-6-ol (16: Compound 15 (120 mg, 0.2 mmol) was dissolved with MeOH (2 mL) and treated with 1 M solution of NaOMe (600 mL, 3 eq) at r.t. for 1 h. The solvent was removed and the residue was diluted with EtOAc, washed with $H_2O$ and brine, and dried over $Na_2SO_4$. Plurification by column chromatography using 5:1 hexane-EtOAc as an eluent gave 16 (107 mg, 96%), $[α]_D$ −5.40° (c 1.13, $CHCl_3$).

(4R,5R,6S)-1-tert-butyldimethylsilyoxy-6-[(chloromethylsulfonyl)-oxy]-4,5,7-tribenzyloxy-2(E)-heptene (17): A mixture of compound 16 (1.82 g, 3.23 mmol) and chloromethylsulfonyl chloride (342 mL, 3.83 mmol) in pyridine (14 mL) was stirred at r.t. for 0.5 h. The mixture was diluted with EtOAc, washed with $H_2O$ and brine, and dried over $Na_2SO_4$. After removal of the solvent, the residue was purified by column chromatography (15:1 hexane-EtOAc) to give 17 (1.99 g, 92%) as a colorless oil.

(4R,5R,6S)-6-[(chloromethylsulfonyl)oxy]-4,5,7-tribenzyloxy-2(E)-hepten-1-ol (18): A solution of compound 17 (1.0 g, 1.48 mmol) in THF (5 mL) was treated with 1N HCl (5 mL) at r.t. for 8 h. The THF was removed and the mixture was diluted with EtOAc and the organic layer was washed with aq. $Na_2CO_3$, $H_2O$ and brine. After concentration, the residue was purified by column chromatography (3:1 hexane-EtOAc) to afford 18 (790 mg, 95%) as a colorless oil.

(2S,3R,4S,5R,6S)-6-[(chloromethylsulfonyl)oxy]-2,3-epoxy-4,5,7-tribenzyloxy-2(E)-hepten-1-ol (19a): A solution of Ti(O-i-Pr)$_4$ (365 μL, 1.26 mmol) and L-(+)-diethyltartrate (210 μL, 1.26 mmol) in $CH_2Cl_2$ (4 mL) was stirred at −25° C. for 0.5 h in the presence of MS 4A (activated at 150° C. by microwave oven). To this mixture was added a solution of compound 18 (350 mg, 0.63 mmol) in $CH_2Cl_2$ (1 mL), and the mixture was stirred at the temperature for 0.5 h. A solution of t-BuOOH (5 M, 365 μL, 1.89 mmol) was added and the mixture was stirred at the same temperature for 48 h. A solution of 10% tartaric acid was added at −25° C. and stirred for 0.5 h at the temperature, and for 0.5 h at r.t. The solution was filtered through a Celite pad and the filtrate was washed with $H_2O$ and brine, and the solvent was removed. The residue was dissolved in $Et_2O$ (20 mL) and stirred with 10% NaOH solution at 0° C. for 0.5 h. The organic layer was washed with $H_2O$ and brine, dried and concentgrated. The crude mixture was purified by column chromatography (1:1 hexane-EtOAc) to afford 19a (270 mg, 75%) as a colorless oil.

(2S,3R,4S,5R,6R)-6-azide-2,3-epoxy-4,5,7-tribenzyloxy-2(E)-hepten-1-ol (20a): Compound 19a (225 mg, 0.39 mmol) was dissolved with DMF (3 mL) and treated with NaN₃ (51 mg, 0.78 mmol) at 70° C. for 0.5 h. After cooling to r.t., the mixture was diluted with EtOAc and washed with H₂O and brine, dried and the solvent was removed. The residue was purified by column chromatography (2:1 hexane-EtOAc) to give 20a (157 mg, 82%) as a colorless oil; IR 2200 cm⁻¹.

(1'R,2S,3R,4R,5R)-3,4-dibenzyloxy-5-benzyloxymethyl-2-[1',2'-dihydroxy-ethyl]-pyrrolidine (21a): A solution of compound 20a (1735 mg, 0.36 mmol) and triphenylphosphine (113 mg, 0.43 mmol) in THF (5 mL) containing ca. 0.5% H₂O was stirred at r.t for 48 h. After removal of the solvent, the residual mixture was purified by column chromatography (20:1 CHCl₃-MeOH) to give 21a (137 mg, 82%).

(2R,3S,4R,5R,1'R)-5-hydroxymethyl-3,4-dihydroxy-2-(1',2'-dihydroxy)ethyl-pyrrolidine (1): A solution of 21a (58 mg, 0.13 mmol) in MeOH (1 mL) was stirred with Pd/C under H₂ atmosphere at r.t. for 48 h. The crude material, obtained after removal of the catalyt and solvent, was purified by column chromatography (6:4:1 CHCl₃-MeOH—H₂O) to afford 1 (17 mg, 70%); $[\alpha]_D$ +11° (c 0.1, D₂O).

(2R,3S,4S,5R,6S)-6[(chloromethylsulfonyl)oxy]-2,3-epoxy-4,5,7-tribenzyloxy-2(E)-hepten-1-ol (19b): Compound 19b was synthesized using 18 (250 mg, 0.43 mmol), a solution of Ti(O-i-Pr)₄ (260 μL, 0.86 mmol), D-(−)-diethyltartrate (150 μL, 0.86 mmol), a solution of t-BuOOH (5 M, 260 μL, 1.29 mmol), a solution of 10% tartaric acid, MS 4A and CH₂Cl₂ (4 mL, total volume) as described for the synthesis of compound 19a; Yield: 19b (235 mg, 91%), a colorless oil.

(2R,3S,4S,5R,6R)-6-azide-2,3-epoxy-4,5,7-tribenzyloxy-2(E)-hepten-1-ol (20b): Compound 20b was synthesized using 19b (195 mg, 0.34 mmol), NaN₃ (44 mg, 0.68 mmol) and DMF (3 mL) as described for the synthesis of 20a; Yield: 20b (144 mg, 87%), a colorless oil; $[\alpha]_D$ −29.3° (c 1, CHCl₃); IR 2170 cm⁻¹.

(2R,3S,4R,5R,1'R)-5-benzyloxymethyl-3,4-dibenzyloxy-2-(1',2'-dihydroxy)ethyl-pyrrolidine (21b): Compound 21b was synthesized using 20b (3.44 g, 7.03 mmol), triphenylphosphine (2.21 g, 8.44 mmol) and THF (36 mL) as described for the synthesis of 21a; Yield: 21b (2.98 g, 91%).

(1'R,2S,3R,4R,5R)-3,4-dihydroxy-2-[1',2'-dihydroxy-ethyl]-5-hydroxymethyl-pyrrolidine (2): Compound 2 was obtained by hydrogenolysis of 21b (100 mg, 0.2 mmol) was carried out as described for the synthesis of 1 in MeOH (1 mL) to afford 2 (30 mg, 72%); $[\alpha]_D$ +25.6° (c 0.3, D₂O).

(1"R,2R,3R,4R,5R)-N-Butyloxycarbonyl-[3,4-dibenzyloxy-5-benzyloxymethyl-2-(1'2'-dihydroxy-ethyl)]-pyrrolidine (22): To a solution of 21 (336 mg, 0.73 mmol) in CH₂Cl₂ (7 mL) and Et₃N (121 μL, 0.87 mmol), (Boc)₂O (412 μL, 1.74 mmol) was added at 0° C. and the mixture was stirred at r.t. for 20 h. The reaction mixture was diluted with CH₂Cl₂ and washed with 10% citric acid, sat. NaHCO₃, and water, dried over MgSO₄, and concentrated. The resulting material was purified on a column of silica gel eluted with hexane-EtOAc (3:1) to afford 22 (374 mg, 91%), $[\alpha]_D$=−31.3° (c 1.0, CHCl₃).

(2S,3R,4R,5R)-N-Butyloxycarbonyl-(3,4-dibenzyloxy-5-benzyloxymethyl)-pyrrolidine-2-carbaldehyde (23): To a solution of compound 22 (740 mg, 1.3 mmol) in toluene (13 mL), Pb(OAc)₄ (959 mg, 2.0 mmol) was added. The reaction mixture was stirred for 1.5 h at r.t., then diluted with Et₂O, filtered through a Celite pad, and concentrated. The resulting residue was purified on a column of silica gel eluted with 8:1 hexane-EtOAc to afford 23 (684.8 mg, ~quant.); $[\alpha]_D$ −56.6° (c 1.0, CHCl₃). NMR (CDCl₃) analysis showed that 23 existed as two conformational isomers which were designated to be "major" and "minor". Major/Minor=10/7.

(2R,3R,4R,5R)-N-Butyloxycarbonyl-(3,4-dibenzyloxy-5-benzyloxymethyl-2-hydroxymethyl)-pyrrolidine (24): To a solution of 23 (1.17 g, 2.2 mmol) in CH₂Cl₂ (15 mL) cooled to 0° C. was added 0.98 M di-iso-butylaluminum hydride (DIBAL) in hexane (2.7 mL, 2.6 mmol) and the resulting mixture was stirred for 0.5 h until completion. MeOH (1 mL) was added to the mixture and was stirred at r.t. for 0.5 h. The mixture was diluted with Et₂O, washed with brine, dried over MGSO₄, and concentrated to give a syrup, which was purified by flush column chromatography using 4:1 hexane-EtOAc as the eluent to give 24 (1.14 g, 97%); $[\alpha]_D$ −42° (c 1.0, CHCl₃). Major/Minor=20/7.

(2R,3R,4R,5R)-N-Butyloxycarbonyl-(2-azidomethyl-3,4-dibenzyloxy-5-benzyloxymethyl)-pyrrolidine (26) and (2R,3R,4R,5R)-(3,4-dibenzyloxy-5-benzyloxymethyl)-pyrrolidino-[1,2,c]-oxazole-3-one (27): To a solution of compound 24 (371 mg, 0.70 mmol) in CH₂Cl₂ (7 mL) was added MsCl (81 μL, 1.04 mmol) and Et₃N (145 μL, 1.04 mmol) at 0° C. The mixture was stirred at r.t. for 2 h, diluted with EtOAc, washed successively with N HCl, sat. NaHCO₃, water, and brine, then dried over MgSO₄ and concentrated. The resulting syrup was purified on a column of silica gel eluted with 5:1 hexane-EtOAc to give mesyl ester 25 [Rf 0.48 (2:1 hexane-EtOAc); 424 mg, quant.] which was then dissolved in DMF (9 mL). To this solution was added NaN₃ (451 mg, 6.9 mmol), and the mixture was stirred at 70° C. for 35 h. The mixture was concentrated to about half volume and diluted with EtOAc, washed with water, dried over MgSO₄, and concentrated. The residue was purified on a column of silica gel using 9:1 and 3:1 hexane-EtOAc as eluent. The former eluent afforded the desired 26 [Rf 0.76 (2:1 hexane-EtOAc); 253 mg, 65%] (Major/Minor=5/4) and the latter gave oxazolone 27 [Rf 0.32 (2:1 hexane-EtOAc); 94 mg, 28%]. Physical data for compound 26: $[\alpha]_D$ −47.5° (c 1.0, CHCl₃); Complex signals were obtained due to the existance of two conformational isomers at almost 1:1 ratio, and only chemical shifts were reported. Physical data for compound 27: $[\alpha]_D$=+4° (c 1.0, CHCl₃).

(2R,3R,4R,5R)-N-Butyloxycarbonyl-(2-aminomethyl-3,4-dibenzyloxy-5-benzyloxymethyl)-pyrrolidine (28): A mixture of compound 26 (65 mg, 0.12 mmol) and 5% Pd on C (ca. 20 mg) in MeOH (2.5 mL) was stirred under H₂ atmosphere at r.t. for 1.5 h until completion [Rf 0.49 (9:1 CHCl₃-MeOH)]. The reaction mixture was filtered to remove the catalyst, then concentrated to dryness to afford 28 (59 mg, Major/Minor=4/3); $[\alpha]_D$ −48.1° (c 1.6, CHCl₃).

(2R,3R,4R,5R)-N-Butyloxycarbonyl-(2-acetamidomethyl-3,4-dibenzyloxy-5-benzyloxymethyl)-pyrrolidine (29): The amine 28 was acetylated using Ac₂O (30 μL) and Pyr. (2 mL) to yield 29 (55.7 mg, 83%, Major/Minor=10/7) after purification on a column of silica gel using a 20:1 fixture of CHCl₃-MeOH as eluent; $[\alpha]_D$ −4.6° (c 0.5, CHCl₃).

(2R,3R,4R,5R)-2-Acetamidomethyl-3,4-dihydroxy-5-hydroxymethyl-pyrrolidine 3): A solution containing compound 29 (11.7 mg, 0.038 mmol) in MeOH (1.5 mL) was acidified with 0.1N HCl to pH 4–5, and was added a catalytic amount of 5% Pd on C. The reaction mixture was stirred under H₂ atmosphere at r.t. for over night. Filtration and evaporation of the solvent afforded a syrup quantitatively, which was then treated with TFA-H₂O (9:1 v/v, 300 μL) and the solution was kept at r.t. for 1 h. The mixture was neutralized to pH 8 using 28% NH₃ and concentrated. The resulting residue was purified on a column of Iatro Beads using a 9:2:1 mixture of i-PrOH-28% NH₃—H₂O to afford 15 mg of salt form which was treated with Dowex 1×8 (OH⁻) to give 3 (7 mg, 81%). 3 was further purified for the inhibition assay using Sep-Pak PLUS CM, regenerated with M HCl (10 mL) and water (20 mL), eluted with water (20 mL) and 10% $NH_3$—$H_2O$ (10 mL). The latter eluent containing 3 was filtered through a Millex GV filter and lyophilized.

(2R,3R,4R,5R)-2-Acetamidomethyl-3,4-dibenzyloxy-5-benzyloxymethyl-prrolidine (30): Compound 29 (142 mg, 0.25 mmol) was treated with TFA-$H_2O$ (95:5 v/v, 1.2 mL) at r.t. for 2 h. The resulting solution was neutralized with sat. $NaHCO_3$ to pH 7 and extracted with EtOAc. The combined organic layers were dried over $MgSO_4$, filtered, evaporated, and purified on a column of silica gel eluted with $CHCl_3$-MeOH (20:1) to afford 30 (113 mg, 96%); $[\alpha]_D$ +32.3° (c 1.3, $CHCl_3$).

(2R,3R,4R,5R)-M-Methyl-(2-acetamidomethyl-3,4-dibenzyloxy-5-benzyloxymethyl)-pyrrolidine (31): To a solution of 30 (16 mg, 0.034 mmol) in MeOH (0.5 mL) at 0° C. was added 37% formaldehyde solution (5.1 mL, 0.068 mmol) and $NaBH_3CN$ (4.2 mg, 0.068 mmol). The mixture was stirred at r.t. for overnight. The reaction mixture was added $H_2O$, extracted with $CHCl_3$ and dried with $MgSO_4$. After removal of the solvent, the residue was purified by preparative TLC ($CHCl_3$-MeOH 9:1) to yield 31 (12 mg, 71%); $[\alpha]_D$ –10.8° (c 0.3, $CHCl_3$).

(2R,3R,4R,5R)-N-Buthyl-(2-acetamidomethyl-3,4-dibenzyloxy-5-benzyloxymethyl)-pyrrolidine (32): Compound 32 was synthesized according to the procedure described for the synthesis of 31 using n-butanal instead of formaldehyde; Yield: 74%, $[\alpha]_D$ –35° (c 0.56, $CHCl_3$).

(2R,3R,4R,5R)-N-Methyl-(2-acetamidomethyl-3,4-dihydroxy-5-hydroxymethyl-pyrrolidine (4): Compound 31 (18.7 mg, 0.038 mmol) was dissolved in MeOH (1.5 mL), and to this solution was acidified with 0.1N HCl to pH 4–5 and added a catalytic amount of 5% Pd on C. The reaction mixture was stirred under $H_2$ atmosphere at r.t. for overnight. The catalyst was removed by filtration, and the solvent was concentrated under vaccum. The residue was purified on a column of Iatro Beads using a 9:2:1 mixture of i-PrOH-28% $NH_3$—$H_2O$ and treated with Dowex 1×8 (OH⁻) to give 4 (6.6 mg, 80%); $[\alpha]_D$ –26.6° (c 0.5, MeOH).

(2R,3R,4R,5R)-N-Buthyl-(2-acetamidomethyl-3,4-dihydroxy-5-hydroxymethyl)-pyrrolidine (5): Compound 5 was synthesized in 85% from 30 according to the procedure described for the synthesis of compound 4.

(1'R,2R,3R,4R,5R)-N-Butyloxycarbonyl-[3,4-dibenzyloxy-5-benzyloxymethyl-2-(2'-azido-1'-hydroxyethyl)]-pyrroidine (34): To a solution of compound 22 (383 mg, 0.68 mmol) dissolved in Pyr. (7 mL) was added TsCl (194 mg, 1.02 mmol). The reaction mixture was stirred at r.t. for 37 h. $H_2O$ was added to the mixture and stirred for 5 min. The mixture was diluted with EtOAc, washed with N HCl, water, sat. $NaHCO_3$, and brine, dried over $MgSO_4$, and concentrated. The residue was purified on a column of silica gel (4:1 hexane-EtOAc) to give 33 [Rf 0.49 (2:1 hexane-EtOAc); 417 mg, 85%], which was then dissolved in DMF (4 mL) and the solution was added $NaN_3$ (151 mg, 2.33 mmol). The mixture was stirred at 70° C. for 4 h. $H_2O$ was added. After stirring for 5 min, the mixture was diluted with EtOAc, washed with brine, dried over $MgSO_4$, and concentrated. The residue was purified on a column of silica gel using 8:1 hexane-EtOAc as an eluent to afford 34 (235 mg, 69%, Major/Minor=5/2); $[\alpha]_D$ –23.41° (c 1.0, $CHCl_3$).

(1'R,2R,3R,4R,5R)-N-Butyloxycarbonyl-[2-(2'-azido-1'-benzyloxy-ethyl)-3,4-dibenzyloxy-5-benzyloxymethyl]-prrolidine (35): To a solution of 34 (132 mg, 0.22 mmol) in DMF (3 mL) was successively added $Ag_2O$ (208 mg, 0.9 mmol), BnBr (107 μL, 0.9 mmol), and KI (74 mg, 0.45 mmol) at 0° C. The reaction mixture was stirred at r.t. for 7 h, then added $Et_2O$-water and stirred for 10 min. After filtration through a Celite pad, the mixture was extracted with $Et_2O$, the organic layer was separated, dried over $MgSO_4$, and concentrated. The residue was purified on a column of silica gel using 10:1 hexane-EtOAc as an eluent to yield 35 (139 mg, 93%); $[\alpha]_D$ –30.7° (c 1.06, $CHCl_3$).

(1'R,2R,3R,4R,5R)-N-Butyloxycarbonyl-[2-(2'-amino-1'-benzyloxy-ethyl)-3,4-dibenzyloxy-5-benzyloxymethyl]-pyrrolidine (36): To a solution of compound 35 (29 mg, 0.043 mmol) in MeOH (2 mL) was added 5% Pd on C (ca. 20 mg). The mixture was stirred under $H_2$ atmosphere at r.t. for 1 h. Filtration and concentration afforded 36 (25 mg); $[\alpha]_D$ –30.3° (c 0.8, $CHCl_3$).

(1'R,2R,3R,4R,5R)-N-Butyloxycarbonyl-[2-(2'-acetamido-1'-benzyloxy-ethyl)-3,4-dibenzyloxy-5-benzyloxymethyl]-pyrrolidine (37): The amine 36 was redissolved in pyridine (1.5 mL), and $Ac_2O$ (0.5 mL) was added to the solution. The mixture was kept at r.t. for overnight and concentrated to dryness. The residue was purified on preparative TLC using a 10:1 mixture of $CHCl_3$-MeOH as mobile phase to afford 37 (25 mg, 84%); $[\alpha]_D$ +2.6° (c 0.4, $CHCl_3$).

(1'R,2R,3R,4R,5R)-2-(2'-acetamido-1'-hydroxy-ethyl)-3,4-dihydroxy-5-hydroxymethyl-pyrrolidine (6): To a solution of compound 37 (41 mg, 0.059 mmol) in MeOH (1.5 mL), 0.1 N HCl (0.2 mL) and 5% Pd on C (25 mg) were added and the mixture was stirred under $H_2$ atmosphere at r.t. for overnight. Filtration and evaporation of the solvent afforded a syrup quantitatively, which was then treated with TFA-$H_2O$ (9:1) at r.t for 2 h. The mixture was adjusted to pH 8 using $NH_3$ (28%) and concentrated to give a syrup, which was purified on a column of Iatro Beads using a 9:1:2 mixture of i-PrOH—$NH_3$(28%)-$H_2O$ to yield a TFA salt (14.5 mg). The residue was treated with Dowex 1×8 (OH⁻) and eluted with water to give 6 (13.7 mg, quant.); $[\alpha]_D$ +30.6° (c 0.69, MeOH).

(1'R,2R,3R,4R,5R)-2-(2'-acetamido-1'-benzyloxy-ethyl)-3,4-dibenzyoxy-5-benzyloxymethyl-pyrrolidine (38): Compound 38 was synthesized from 37 according to the procedure described for the synthesis of compound 30.

(1'R,2R,3R,4R,5R)-N-Methyl-[2-(2'-acetamido-1'-hydroxy-ethyl)-3,4-dihydroxy-5-hydroxymethyl]-pyrrolidine (7): Compound 7 was synthesized in 86% from 38 according to the procedure described for the synthesis of compound 4.

(1'R,2R,3R,4R,5R)-N-Ethyl-[2-(2'-acetamido-1'-hydroxy-ethyl)-3,4-dihydroxy-5-hydroxymethyl]-pyrrolidine (8): Compound 8 was synthesized in 83% from 38 according to the procedure described for the synthesis of compound 4.

N,N-Di-{[(2R,3R,4R,5R)-(3,4-dibenzyloxy-5-benzyloxymethyl)-pyrrolidine]methyl}amine (39): Ammonium acetate (59 mg, 0.77 mmol) was added to a solution of aldehyde 23 (41 mg, 0.077 mmol) in MeOH (1 mL), then sodium cyanoborohydride (5.3 mg, 0.085 mmol) was added to the solution at r.t. The mixture was stirred for 22 h, then concentrated and extracted with $CHCl_3$. The organic layer was washed with sat. $NaHCO_3$ and $H_2O$, and dried over $MgSO_4$. The solvent was evaporated in vacuo and the residue was purified by preparative TLC (2:1 hexane-EtOAc) to give 39 [Rf 0.46 (2:1 hexane-EtOAc); 30.4 mg, 75%]; $[\alpha]_D$ –58° (c 0.75, $CHCl_3$).

N-Butyloxycarbonyl-N,N-di-{[(2R,3R,4R,5R)-(3,4-dibenzyloxy-5-benzyloxymethyl)-pyrrolidine]methyl}amine (40) and N,N-di-{[(2R,3R,4R,5R)-(3,4-hydroxy-5-hydroxymethyl)-pyrrolidine]methyl}amine (9):

To a solution of 39 (32 mg, 0.03 mmol) in $CH_2Cl_2$ (2 mL) and $Et_3N$ (5 μL, 0.036 mmol), $(Boc)_2O$ (17 μL, 0.073 mmol) was added at 0° C. and the mixture stirred at r.t. for overnight. The reaction mixture was diluted with $CH_2Cl_2$ and was washed with 10% citric acid, sat. $NaHCO_3$, and water, dried over $MgSO_4$, and concentrated. The resulting material was purified by preparative TLC (2:1 hexane-EtOA) to afford 40 [Rf 0.69 (2:1 hexane-EtOAc), 33 mg, 97%]. To the solution of compound 40 (18 mg, 0.016 mmol) dissolved in MeOH (1.5 mL), acidified to pH 4–5 with 0.1N HCl, was added 5% Pd on C (ca. 10 mg). The mixture was stirred under $H_2$ atmosphere at r.t. for over night. The catalyst was filtered off and the filtrate was concentrated. The residue was treated with $TFA-H_2O$ (9:1, 300 μL) at r.t. for 3 h. The mixture was adjusted to pH 8 using $NH_3$ (28%) and concentrated to leave a syrup, which was purified on a column of Iatro Beads using 9:1:2 i-PrOH—$NH_3$(28%)-$H_2O$. The obtained material was finally treated with Dowex 1×8 ($OH^-$) eluted with water to give 9 after concentration (4.6 mg, 94%); $[\alpha]_D$ +55° (c 0.42, MeOH).

3-(E)-2-Azido-4-phenyl-1-butenol (110): NaH (11 g, 95% mineral oil dispersion) was washed with hexane and dried over vacuum. Under argon, dry THF (220 ml) and dry DMSO (220 ml) were added and the reaction mixture was cooled in ice/salt bath. A solution of trimethylsulfonium iodide (84.86 g) in 300 ml DMSO was added over 10 min. After the addition was complete. Trans-cinnamaldehyde 108 (18.5 g) was added in one portion. The reaction mixture was stirred at 0° C. for 40 min and at room temperature for additional 2 h. The reaction mixture was slowly quenched with 800 ml water and ice and extract with methylene chloride (4(500 ml). The combined organic layer were washed with water (2(500 ml), dried over $K_2CO_3$, filtered, and concentrated to afford a brown liquid. Without purification, the liquid was dissolved in 220 ml acetone and 110 ml water, 20 g $NaN_3$ was added, and then the mixture was refluxed gently for 3 h. The reaction mixture was acidified by the addition of ammonium chloride (5.0 g) and stirred for an additional 1 min at room temperature. Water (50 ml) was added, and the acetone was removed in vacuum. The aqueous residue was extracted with methylene chloride, dried over $Na_2SO_4$, filtered, and concentrated. Purified by silica gel chromatography (hexane/ethyl acetate=5:1) to yield 24.2 g yellow liquid 110 (82% from 109).

Mesylation of compound 110: To a solution of 20 g 110 in 100 ml pyridine was added MsCl 9.8 ml, and the mixture was stirred at room temperature for 1.5 h, The reaction mixture was extracted with methylene chloride. After routine work up, flash chromatography (hexanes/EtOAc=4:1) afforded 31.0 g(96%) of 111.

(E)-1-amine-2-aizde-4-phenyl-3-butene 112; An ethanol solution (200 ml) of 111 (16.5 g) was slowly added to a suspension of 9.52 g hexamethylenetetraamine and 10.2 g NaI. The reaction mixture was stirred for 4 days. The precipitate (26 g) that appeared were collected by filtration and was used directly to the next reaction. To the precipitates was added 270 ml ethanol, 27 ml 12N hydrochloric acid. The mixture was heated at 65° C. for 2 min. After the reaction was complete, the white precipitate was removed by filtration. The filtrate was adjusted to pH 8.0 with 10% NaOH and extracted with EtOAc. The organic layer was washed with water and dried over $MgSO_4$ and concentrated. A small portion of the residue was purified by silica gel chromatography ($CHCl_3$/MeOH=20:1).

(E)-N-acetyl-2-azide-4-phenyl-3-butene 113; 300 ml isopropenyl acetate was added to the solution of 12.4 g 112 in 200 ml EtOAc, and the mixture was stirred for overnight at room temperature. After the reaction was complete, the organic solvent was removed under vacuum and the residue was purified by silica gel chromatography (Hexanes/EtOAc=1:1) to yield 113 11.7 g (85% from 111).

Compound 115a and 115b: Under −78° C., a mixture containing 1.50 g 113 in 200 ml methanol was injected ozone gas until the color of the solution of the reaction mixture became pale blue. After bubbling Ar to remove excess amounts of ozone, the ozonide was treated with DMS (35 ml) for 1 day. Methanol was evaporated and the residue was used directly in the next step without purification. To the aqueous solution of the aldehyde was added 5 ml DHAP (424 mM), and the pH was adjusted to 6.5 with 1N HCl. Rabbit muscle FDP aldolase(1000 units) was added to this solution and the mixture was stirred slowly at room temperature until DHAP was consumed completely based on the enzymatic assay[20]. The mixture was passed through AG 1(8 resin ($HCO^{2-}$) (2.4(50 cm) and eluted with water(1 L) 0.1M NaCl(1 L), and 0.4M NaCl(1 L) solution, successively. The pH value of the faction of 0.4M NaCl solution was adjusted to 4.7 with 1N HCl, 1000 units acid phosphatase (from sweet potato, type X) was added, and the mixture was stirred slowly at 37° C. for 1 day. The pH was adjusted to 7.0 and the water was removed under reduced pressure. The residue was treated with MeOH, and the soluble portion was collected and purified by silica gel chromatography ($CHCl_3$/MeOH/$H_2O$=10:1:0.1) to yield 230 mg 115a (44% yield based on DHAP) and 156 mg 115b (30% yield based on DHAP).

Compound 3 or 103: A solution of compound 115a 24 mg or 115b 14 mg in 3 ml ethanol was hydrogenated with 10% Pd/C (5 mg) under 50 psi of hydrogen for 1 day. The catalyst was removed by filtration and the solvent was evaporated under vacuum. The residue was purified by silica gel chromatography ($CHCl_3$/MeOH/$H_2O$=6:4:0.7)) to yield 16 mg 3(80%) or 9 mg 103(80%).

N-methyl five-membered ring iminoclyclitols 4, 104: A solution containing 30 mg of 3 or 103, formaldehyde(300 ul, 37%wt solution), and 10 mg of 10% Pd—C was hydrogenated under 50 psi of hydrogen in 5 ml of methanol/water (1:1 solution) for 24 h, the solvent was removed under reduced pressure, Silica gel chromatography($CHCl_3$/MeOH/$H_2O$=6:4:0.7) afforded 4 or 104 29 mg (90%) respectively.

1-Azido-5(R)-(Benzyloxymethyl)-3(R),4(R)-bis (benzyloxy)-2(S)-(hydroxymethyl)-N-methyl-pyrrollidine (118): 170 mg of 117 and 122 ul pyridine was dissolved in 5 ml methylene chloride, under 0° C. degree, 11 ul MsCl was added. The reaction mixture was stirred for 2 h at room temperature. The solvent was removed under high vacuum. Without purification, The residue was dissolved in 20 ml DMF, 200 mg $NaN_3$ and 60.5 mg NaI were added to this solution. The reaction mixture was stirred at room temperature for 5 h. Extracted with methylene chloride. After routine work up, silica gel chromatography(hexanes/EtOAc=2:1) afforded 156 mg (87%) azide 118.

1-N-Acetyl-5(R)-[(Benzyloxymethyl)-3(R),4(R)-bis (benzyloxy)-2(S)-(hydroxymethyl)-N-methyl-pyrrollidine (19): To the mixture of 104 mg (220 mmol) 118 in 10 ml dry THF was added 118 mg PPh3 (450 mmol). The mixture was heated to 50° C. for 4 h, and concentrated under reduced pressure. The residue was dissolved in 8 ml pyridine, under 0° C., 91 ul $Ac_2O$ was added to the reaction mixture. 12 hours later, 50 ml water was added to the reaction mixture, and extracted with $CH_2Cl_2$. The organic layer was dried over $MgSO_4$ and concentrated under reduced pressure. Purified by silica gel chromatography ($CH_2Cl_2$/MeOH=60:1) to get 119 91 mg (87% yield from 118).

Compound 104: 34 mg 19 was dissolved in 6 ml AcOH/THF/H$_2$O (4:2:1), 10 mg Pd—C (10%) was added to the solution. The reaction mixture was hydrogenated under the pressure of 50 psi. After 1 day, the catalyst was filtered off, and the filtrate was concentrated and purified by silica gel chromatography (CHCl$_3$/MeOH/H$_2$6:4:0.7) to yield 16.6 mg 4(89%). The spectra is same as before.

2-O-acetyl-3-azido-diethyl-propanal 121: To a stirred suspension of 4.52 g KHCO$_3$ in 150 ml methanol was added 45 ml acrolein diethyl acetal, 30 ml benzonitrile, and 32 ml 30% H$_2$O$_2$. The solution was warmed to 40° C. in a water bath. After 8 h, 10 ml of H$_2$O$_2$ was added, after an additional 8 h, 10 ml more H$_2$O$_2$ was added. The solution was allowed to react for an additional 20 h and then 39 g NaN$_3$ was added. The pH was adjusted to 7.5 with 1M H$_2$SO$_4$ and the mixture was maintained at that pH by adding 1M H$_2$SO$_4$ with a peristaltic pump. The solution was warmed to 30° C. for 14 h. After the reaction finished, the methanol was removed under reduced pressure. After 100 ml water was added, the solution was extracted with methylene chloride. The organic layer was washed with brine, dried over Na$_2$SO$_4$, and then evaporated to remove the solvent. Hexane was added to precipitate benzamide. The mixture was filtered and the filtrate was evaporated under reduced pressure. The residue was dissolved in 36.4 ml pyridine and reacted with 34 ml Ac$_2$O. After 3 h at room temperature, 8 ml methanol was added to quench the excess Ac$_2$O. 150 ml ethyl acetate was added, and then washed with water, 1N HCl, saturated NaHCO$_3$, and brine and dried over Na$_2$SO$_4$. Filtered and concentrated. Distillation of the residue yielded 52.5 g of 121 (76%).

3-azido-1-ol-diethyl propanal 122: A solution of 2.31 g 121 in 100 ml of phosphate buffer solution (0.05M, pH7.0) was mixed with 100 mg PS-80 at room temperature with stirring. The pH was maintained at 7.0 with a peristatic pump by adding 0.25N NaOH and the degree of conversion was monitored by the consumption of base. After 49% conversion, the reaction mixture was extracted with EtOAc. After routine work up, Flash chromatography (EtOAc/hexanes=1:10) afforded 1.0 g (45%) of the wanted enantiomer 122.

(R)-N-acetyl-2-diethoxymethylaziridine 124: To a 500 ml flask containing 20 ml anhydrous toluene and 1.0 g 122 was added 2.62 g triphenylphosphine. The solution was stirred at room temperature until bubbling of N$_2$ stopped. The mixture was then heated to 120° C. for 3 h. The solvent was removed under reduced pressure. Without further purification, the mixture was put to 30 ml CH$_2$Cl$_2$ containing 10.0 g of K$_2$CO$_3$. To this mixture was added 1.0 ml of acetic anhydride. The mixture was stirred at room temperature for 15 h. The mixture was filtered and the solvent was removed under reduced pressure. The residue was purified by silica gel chromatography to yield 0.280 g of 124 (30% yield).

(R)-3 Azido-2-acetamidopropanal Diethyl Acetal 125: A mixture containing 3.26 g of 124 and 15 g of sodium azide in 140 ml of DMF was added 140 ml of ZnCl$_2$ (1.0M solution in Et$_2$O). The mixture was stirred at 75° C. for 3 days and then extracted with EtOAc. The organic layer was washed with water, dried over MgSO$_4$ and concentrated. The residue was purified by silica gel chromatography (hexane/EtOAc=3:2) to yield 2.52 g of 125 (62%).

Compound 126: A mixture containing 500 mg of 125 and 15 ml of HCl buffer (pH=1) was heated to 45° C. for 10 h. A solution of DHAP (1.7 ml, 424 mM) was then added, and the pH was adjusted to 6.5 with 1N NaOH. To this solution, rabbit muscle FDP aldolase (250 units) was added, and the mixture was stirred slowly at room temperature until DHAP was consumed completely based on enzymatic assay[20]. The mixture was passed through AG-1(8 resin(HCO$^{2-}$) (2.415 cm) and eluted with water (200 ml), 0.1M NaCl (150 ml), 0.4M NaCl (300 ml) successively. After adding 100 ml of water to the fraction eluted by the 0.4M NaCl, the pH was adjusted to 4.7 with 1N HCl and 600 units acid phosphatase (from sweet potato, type X) was added, and the mixture was shaken slowly at 37° C. for 1 d. The pH was adjusted to 7.0, and water was removed by evaporation. The residue was treated with methanol. The soluble portion was collected and purified by silica gel chromatography (CHCl$_3$/MeOH/H$_2$O=8:2:0.1) to yield 34 mg(55%) of 126.

1,2-Dideoxy-2-acetamidonojirimycin 105: To a solution of 30 mg of 126 in 5 ml of EtOH was added 10 mg of Pd—C, and the mixture was hydrogenated under the pressure of 50 psi. After 1 day, the catalyst was filtered off, and the filtrate was concentrated and purified by silica gel chromatography (CHCl$_3$/MeOH/H$_2$)=6:4:0.7) to yield 21 mg(87%) of 105.

N-Methyl-1,2-Dideoxy-2-acetamidonojirimycin 106: A solution containing 10 mg of 105, formaldehyde (300 ul, 37%wt solution), and 10 mg of 10% Pd—C was hydrogenated under 50 psi of hydrogen in 5 ml of methanol/water (1:1 solution) for 24 h. The solvent was removed under reduced pressure. Silica gel chromatography (CHCl$_2$/MeOH/H$_2$O=6:4:0.7) afforded 106 10 mg (92%).

2-acetamido-2 deoxy-3,4,6-tri-O-acetyl-thiozoline 128: A solution of 1.0 g of 2-acetamido-2 deoxy-1,3,4,6-tetra-O-acetyl-β-D-glucopyranose 127 in 10 ml of toluene was treated with 0.68 g of Lawesson's reagent, and the reaction mixture was heated at 800° C. for 1.5 h, cooled, and then concentrated. The residue was chromatographed on the silica gel chromatography (EtOAc/methylene chloride=3:7) to yield 0.89 g (100%) of 128.

NAG-thiozoline 107: The thioazoline triacetate (0.22 g) 128 dissolved in 3 ml methanol was treated with 70 ul of 25% w/w methanolic sodium methoxide and the reaction mixture was stirred at room temperature for 30 min. The reaction was neutralized to pH7.0 with H-from resin, and then concentrated to a solid residue. Extracted with methylene chloride, and the organic layer was concentrated. Flash chromatography(methylene chloride/methanol=4:1) afforded a white solid 117 mg(85%) of the thioazoline 107.

Sulfated NAG-thiozoline 108: To a solution of 55 mg 107 in the 4 ml pyridine was added 35 mg SO$_3$(NMe$_3$. The mixture was first stirred under 0° C. for 2 h, and then stayed at room temperature overnight. After concentration, silica gel chromatography (methylene:chloride/methanol=4:1) afforded 78 mg(87%) 108.

Silyl ether 203: To a 1.2 ml DMF solution containing 70 mg(0.32 mmol) iminocyclitol 3 was added 84 ul(0.48 mmol) triethylamine and then cooled to 0° C., 72 mg TBDMSCl (0.46 mmol) was added and this mixture was stirred for overnight at room temperature. After the reaction finished, the solvent was removed under vacuum and the residue was purified by silica gel chromatography(CH$_3$Cl/MeOH=9:1) to afford the silyl ether 203 93 mg(88% yield).

6-OH iminocyclitol 205: A solution of 7 mg 203(0.02 mmol) in 2 ml pyridine was cooled down to 0° C. and then 0.1 ml Ac$_2$O was added. The mixture was stirred for 5.0 hrs at room temperature. The solvent was then removed under vacuum and dried further under high vacuum. The crude silyl ether 204 residue was dissolved in a mixture solvent (AcOH/H$_2$O/THF=5:1:3). The reaction mixture was stirred for overnight at 50° C. After the reaction was completed, the solvent was removed under vacuum and the residue was purified by silica gel chromatography (EtOAc/MeOH=4:1) to yield 205 4.5 mg (75% from 203).

Sulfation of compound 205: Under argon protection, 15 mg SO$_3$(pyridine complex and 3 mg(0.01 mmol) compound 205 was dissolved in 0.5 ml pyridine. The mixture was stirred for overnight at room temperature. After no starting material was left, the solvent was removed and the residue was purified by silica gel chromatography (EtOAc/MeOH= 2:1) to afford 3.1 mg 206 (82%).

6-Sulfate α-iminocyclitols 207: 2 mg(0.005 mmol) protected 6-sulfate α-iminocyclitol 206 was dissolved in 2 ml MeOH and then 2 drops of the 25% MeONa was added to the solution. The reaction was completed in 30 minutes and was quenched by acidic resin(H$^+$). The solvent was then removed and the residue was purified by reverse phase column (Lichroprep RP-18) to afford 13 mg 207 (85%).

6-Silyl ether protected β-iminocyclitol 208: 45 mg(0.2 mmol) β-iminocyclitol 202 and 60 ul triethylamine(0.4 mmol) were dissolved in 2 ml DMF. The mixture was cooled down to 0° C. 71 ul(0.3 mmol) of TBDMSOTf was then added dropwise to the reaction system. The reaction was completed in 1.0 hour. After removal of the solvent, the residue was purified by silica gel chromatography (CH$_3$Cl/MeOH=10:1) to afford 62 mg 208 (90%).

Benzylation of 208: 70 mg(0.21 mmol) of silyl ether 208 was dissolved in 3 ml DMF under the protection of argon, the solution was then cooled to 0° C., 24 mg 60% NaH(0.56 mmol) was added. The mixture was stirred for 10 minutes before 101 ul BnBr(0.46 mmol) was added. The temperature was then increased to 25° C. The reaction was completed after 12 hours. The reaction mixture was then poured into 20 ml ice-water. The resulted mixture was extracted with EtOAc. The organic phase was then dried over anhydrous Na$_2$SO$_4$ and concentrated. The residue was purified by silica gel chromatography (hexane/EtOAc=1:2) to afford 97 mg fully protected iminocyclitol 209 (90%).

6-OH β-iminocyclitol 210: 25.8 mg(0.05 mmol) 209 was dissolved in 3 ml THF. The mixture was cooled down to 0° C. 76 ul TBAF solution (1.0M in THF) was added dropwise. The mixture was stirred for 4 hours at room temperature until the reaction was completed. The solvent was removed and the residue was purified by silica gel chromatography (MeOH/EtOAc=1:10) to give 16 mg 10 in 80% yield.

Sulfation of 210: 14 mg 210 (0.035 mmol) and 56 mg SO$_3$(Pyridine (10 eqiv.) were dissolved in 2 ml pyridine. The mixture was stirred for overnight at room temperature. After the reaction was completed, the solvent was removed and the residue was purified by silica gel chromatography (MeOH/EtOAc=1:4) to afford 13 mg 211(80%).

6-Sulfate β-iminocyclitols 212: 20 mg(0.042 mmol) benzyl ether protected iminocyclitol 211 was dissolved in 3 ml MeOH—H$_2$O(1:1) 30 mg Pd(OH)/C was added. The mixture was hydrogenated under 1.0 atm H$_2$ pressure for 12 hours. After the reaction was completed, the solvent was removed and the residue was purified by silica gel chromatography (CH$_3$Cl/MeOH/H$_2$O=6:4:0.7) to afford 9.3 mg 212 (75%).

Methylation of 6-sulfated 3,4-diacetyl α-iminocyclitol 206: 5 mg(0.013 mmol) 206 was dissolved in 2 ml MeOH and the mixture was stirred for 1.0 hour at 50° C. until the reaction was completed. The solvent was removed and the residue was purified by silica gel chromatography (EtOAc/MeOH=2:1) to afford 4.6 mg 215 (90%).

6-Sulfate methyl ester α-iminocyclitols 216: 2 mg(0.005 mmol) protected 6-sulfate methyl ester 215 was dissolved in 2 ml MeOH and then 2 drops of the 25% MeONa was added to the solution. The reaction was completed in 30 minutes and was quenched by acidic resin(H$^+$). The solvent was then removed and the residue was purified by reverse phase column (Lichroprep RP-18) to afford 1.3 mg 216 (80%).

Enzymatic Assay

Materials: The source of enzymes and substrates are as follows. α-glucosidase (EC 3.2.1.20) from Saccharomyces sp. and β-glucosidase (EC 3.2.1.21) from Sweet almond: Toyobo Co., Ltd. (Osaka, Japan); β-N-Acetylglucosaminidase (EC 3.2.1.30) from bovine kidney and β-N-acetylhexosaminidase A and P (EC 3.2.1.52) from human placenta: Sigma Chemical Co. (St. Louis, Mo., USA); p-nitrophenyl-α-D-glucopyranoside and p-nitrophenyl-β-D-glucopyranoside; p-Nitrophenyl 2-N-acetyl-2-deoxy-β-D-glucopyranoside (p-nitrophenyl-N-acetyl-β-glucosaminide or p-NP-GlcNAc): Seikagaku Kogyo Co., Ltd (Tokyo, Japan); sodium acetate, sodium dihydrogenphosphate and sodium hydrogenphosphate: Nacalai Tesque. Inc. (Kyoto, Japan). Double deionized water was prepared from a Milli-Q system from Millipore Corp. (Milford, Mass., USA). Millex-GV syringe filters (0.22 μm×4 mm i.d.) were purchased from Nibon Millipore Ltd. (Yonezawa, Japan).

Kinetic analisis of α-glucosidase: To a 1-mL disposable cuvette was added 950 μL of 0.1 M phosphate buffer (pH 7.0) solution, 20 μL of inhibitor solution, and 20 μL of 20 mM p-nitrophenyl-α-D-glucopyranoside solution. The solution was well mixed and warmed at 37° C. for 5 min, then 20 μL of the enzyme solution in 10 mM phosphate buffer (pH 7.0) containing 0.2% of BSA was added. The reaction was monitored at 400 nm on Beckmann DU-70 spectrophotometer for 15 seconds, and the initial rate of hydrolysis was calculated. The same procedure was repeated with three other substrate concentrations. After the initial rates were accumulated, the corresponding Lineweaver-Burk plot at that inhibitor concentration was constructed.

Kinetic analyssis of β-glucosidase: To a 1-mL disposable cuvette was added 950 μL of 0.1 M acetate buffer (pH 5.0) solution, 20 μL of inhibitor solution, and 20 μL of 20 mM p-nitrophenyl-β-D-glucopyranoside solution. The solution was well mixed and warmed at 37° C. for 5 min, then 20 μL of the enzyme solution, which was dissolved in ice-cold Tris-HCl buffer (pH 7.8) and diluted with 10 mM phosphate buffer (pH 7.0) containing 0.2% of BSA, was added. The reaction was monitored at 400 nm on a Beckmann DU-70 spectrophotometer for 15 seconds, and the initial rate of hydrolysis was calculated. The same procedure was repeated with three other substrate concentrations. After the initial rates were accumulated, the corresponding Lineweaver-Burk plot at that inhibitor concentration was constructed.

Capillary Zone Electrophoresis

Condition of capillary zone electrophoresis: Assays were performed on a Waters Quanta 4000E capillary electrophoresis system, which was equipped with a 53 cm×75 μm fused i.d. silica capillary. Detection was carried out by on-column measurement of u.v. absorption at 405 nm at 7.5 cm from the cathode. The capillary used was pretreated or regenerated with 0.1 M KOH (2 min) and elution buffer before each injection. Samples were loaded by means of hydrostatic pressure at 10 cm height for 30 sec (ca 38.4 nl). Electrophoresis was performed at 20 kV using 50 mM sodium borate (pH 9.2 for β-N-Acetylglucosaminidase assays, pH 9.4 for β-glucosidase assays, pH 10.2 for α-glucosidase and β-N-acetylhexosaminidase assay) as electrolyte at a constant temperature of 37° C. Pherograms were recorded on Millennium 2010 system from Millipore Corp.

Kinetic analysis of β-N-acetylglucosaminidase: Incubations were performed in a total volume of 50 μL. Unless otherwise stated, reaction mixtures contained 25 mM citrate buffer (pH 4.4), various amount of p-NP-GlcNAc (0.5–2.0 mM) and various amount of inhibitors with 6.25 mU of β-N-acetylglucosaminidase. After preincubation for 10 min at 37° C., the reaction was started by the addition of β-N-acetylglucosaminidase and the reaction mixture was incubated for 10 min at 37° C. Then the reaction was terminated by addition of 100 μL of 50 mM sodium borate.

Kinetic analysis of β-glucosidase: The procedure is same as that described for the analysis of β-N-acetylglucosaminidase except for the pH of reaction mixtures (pH 5.5), the substrate p-NP-Glc (0.5–4.0 mM), and the enzyme β-glucosidase (12.8 mU).

Kinetic analysis of α-glucosidase: The procedure is same as that described for the assay of β-Gnase except for the pH of the reaction mixture (phosphate buffer pH 7.0), the substrate [p-NP-α-Glc (0.2–1.1 mM)], and the enzyme [α-glucosidase (5 mU)]. The termination of the reaction was carried out by addition of 50 μL of 200 mM $Na_2CO_3$.

Kinetic analysis of β-N-acetylhexosaminidase from human placenta: Incubations were performed in a total volume of 20 μL. Unless otherwise stated, reaction mixtures contained 100 mM citrate buffer (pH 4.5), various amount of p-NP-GlcNAc (0.1–1.1 mM) and various amount of inhibitors with 3.35 mU of β-N-acetylhexosaminidase A and 1.76 mU of β-N-acetylhexosaminidase P. After preincubation for 10 min at 37° C., the reaction was started by the addition of β-N-Acetylglucosaminidase and the reaction mixture was incubated for 15 min at 37° C. Then the reaction was terminated by addition of 20 μL of 0.2 M sodium carbonate.

What is claimed is:

1. An inhibitor of hexoaminidase or glycosidase represented by the following structure:

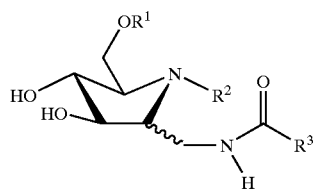

wherein $R^1$ is a sulfate group; $R^2$ is hydrogen, methyl, ethyl or any branched or unbranched hydrocarbon of between 3 and 8 carbon atoms; $R^3$ is a hydrocarbon group that has between 1 and 20 carbon atoms.

2. An inhibitor according to claim 1 wherein $R^3$ is a hydrocarbon group possessing between 1 and 8 carbon atoms.

3. An inhibitor according to claim 2 wherein $R^3$ is methyl.

4. An inhibitor of hexoaminidase or glycosidase represented by the following structure:

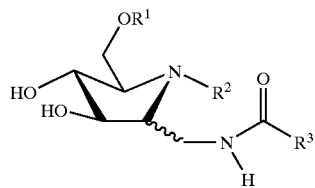

wherein $R^1$ is a methyl sulfate group; $R^2$ is selected from the group consisting of hydrogen, methyl, ethyl, and a branched or unbranched hydrocarbon of between 3 and 8 carbon atoms: $R^3$ is a hydrocarbon having between 1 and 20 carbon atoms.

5. An inhibitor according to claim 4 wherein $R^3$ s a hydrocarbon having between 1 and 8 carbon atoms.

6. An inhibitor according to claim 5 wherein $R^3$ is methyl.

7. An inhibitor of hexoaminidase or glycosidase represented by the following structure:

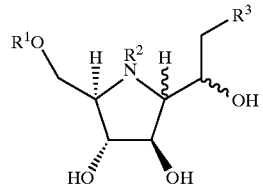

wherein $R^1$ is sulfate; $R^2$ is selected from the group consisting of hydrogen, methyl, ethyl, and a branched or unbranched hydrocarbon of between 3 and 8 carbon atoms; and $R^3$ is —$NHC(O)R^4$, wherein $R^4$ is a hydrocarbon having between 1 and 20 carbon atoms.

8. An inhibitor according to claim 7 wherein $R^4$ is a hydrocarbon having between 1 and 8 carbon atoms.

9. An inhibitor according to claim 8 wherein $R^4$ is methyl.

10. An inhibitor of hexoaminidase or glycosidase represented by the following structure:

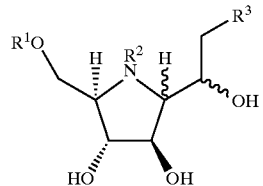

wherein $R^1$ is methyl sulfate; $R^2$ is selected from the group consisting of hydrogen, methyl, ethyl, and a branched or unbranched hydrocarbon of between 3 and 8 carbon atoms; and $R^3$ is —$NHC(O)R^4$, wherein $R^4$ is a hydrocarbon having between 1 and 20 carbon atoms.

11. An inhibitor according to claim 10 wherein $R^4$ is a hydrocarbon having between 1 and 8 carbon atoms.

12. An inhibitor according to claim 11 where $R^4$ is methyl.

13. A process for treating a subject having arthritis comprising the step of administering an inhibitor as in any one of claims 1, 4, 7, and 10 to said subject of sufficient quantity for inhibiting hexoaminidase activity within said subject.

* * * * *